US006469162B1

(12) United States Patent
Winchell et al.

(10) Patent No.: US 6,469,162 B1
(45) Date of Patent: Oct. 22, 2002

(54) COMPOUNDS WITH CHELATION AFFINITY AND SELECTIVITY FOR FIRST TRANSITION SERIES ELEMENTS: USE IN MEDICAL THERAPY AND DIAGNOSIS

(75) Inventors: Harry S. Winchell, Lafayette, CA (US); Joseph Y. Klein, Haifa (IL); Elliot D. Simhon, Haifa (IL); Rosa L. Cyjon, Haifa (IL); Ofer Klein, Haifa (IL); Haim Zaklad, Haifa (IL)

(73) Assignee: Concat, Ltd., Condorc, CA (US)

( * ) Notice: Subject to any disclaimer, the term of this patent is extended or adjusted under 35 U.S.C. 154(b) by 0 days.

(21) Appl. No.: 09/664,952

(22) Filed: Sep. 19, 2000

Related U.S. Application Data

(60) Division of application No. 09/104,695, filed on Jun. 25, 1998, now Pat. No. 6,165,996, which is a division of application No. 08/669,698, filed on Jun. 24, 1996, now Pat. No. 5,874,573, which is a continuation-in-part of application No. 08/560,626, filed on Nov. 20, 1995, now abandoned

(60) Provisional application No. 60/000,524, filed on Jun. 26, 1995.

(51) Int. Cl.[7] .................. C07D 225/00; C07D 225/02
(52) U.S. Cl. .................. 540/474; 540/470; 540/472; 540/473
(58) Field of Search .................. 514/183, 79, 80, 514/338, 340, 406, 422; 540/474, 470, 472, 473

(56) References Cited

U.S. PATENT DOCUMENTS 5,082,851 A * 1/1992 Appelbaum et al. ........ 514/332
5,386,028 A * 1/1995 Tilstam et al. .............. 540/474
5,874,573 A * 2/1999 Winchell et al. ............ 540/465

* cited by examiner

Primary Examiner—Richard L. Raymond
(74) Attorney, Agent, or Firm—Townsend and Townsend and Crew, LLP

(57) ABSTRACT

This invention involves synthesis and use of a class of compounds with chelation affinity and selectivity for first transition series elements. Administration of the free or conjugated compound, or physiological salts of the free or conjugated compound, results in decrease in the in vivo bioavailability of first transition series elements and/or removal from the body of first transition series elements and elements with similar chemical properties. These characteristics make such compounds useful in the management of diseases associated with a bodily excess of first transition series elements and elements with similar chemical properties. This invention demonstrates that such compounds inhibit mammalian, bacterial, and fungal cell replication and are therefore useful in the treatment of neoplasia, infection, inflammation, immune reponse, and in termination of pregnancy. Since these compounds are capable of descreasing the in vivo availability of tissue iron they are useful in management of free radical mediated tissue damage, and oxidation mediated tissue damage. When combined with radioisotopic or paramagnetic cations of first transition series elements, or elements with chemical properties similar to those of first transition series elements, prior to their administration, the resulting complexes are useful as diagnostic agents in nuclear medicine and magnetic resonance imaging (MRI).

2 Claims, No Drawings

COMPOUNDS WITH CHELATION AFFINITY AND SELECTIVITY FOR FIRST TRANSITION SERIES ELEMENTS: USE IN MEDICAL THERAPY AND DIAGNOSIS

CROSS REFERENCE TO RELATED APPLICATION

This application is a division of and claims the benefit of application Ser. No. 09/104,695 filed Jun. 25, 1998, now U.S. Pat. No. 6,165,996, which is a division of application Ser. No. 08/669,698 filed Jun. 24, 1996, now U.S. Pat. No. 5,874,573, which is a continuation-in-part of application Ser. No. 08/560,626 filed Nov. 20, 1995, now abandoned and which claims benefit of provisional application No. 60/000,524 filed Jun. 26, 1995.

This application is related to provisional application No. 60/000,524, filed Jun. 26, 1995, and applications Ser. Nos. 08/543,425 and 08/405,562, each of which is incorporated by reference herein for all legal purposes to be served thereby.

The present invention lies in the field of metal cation chelators (ligands) and their use for purposes of decreasing the bioavailability of elements of the first transition series, and/or the removal from the body of these elements or those with similar chemical properties. First transition series elements are components of enzymes required for nucleic acid replication as well as general cell replication. By inhibiting nucleic acid replication these agents are useful in inhibiting growth of DNA and RNA viruses. By inhibiting bacterial and fungal cell replication these agents are useful in vitro as preservatives, and employing topical or systemic in vivo administration they are useful in treating bacterial and fungal infections and in wound care. By inhibiting protozoan cell replication these agents are useful in treatment of protozoan infections. By inhibiting mammalian cell replication, these agents are useful in treating neoplastic disease, in suppression of the immune response, in inhibition of osteoclast activity, and in termination of pregnancy. Iron, a first transition element, is involved in free radical mediated tissue damage. By decreasing the body free iron content, these agents inhibit free radical mediated tissue damage. Excess of body iron characterizes hemochromatosis/-hemosiderosis, and excess of the first transition series element, copper, characterizes Wilson's disease. By removing either excess iron or copper from the body these agents are useful in treating these diseases. When combined with elements possessing paramagnetic properties, the chelating agents described herein also find diagnostic utility as contrast enhancing agents in magnetic resonance imaging. When combined with radioactive elements, these chelating agents find utility in nuclear medical imaging.

BACKGROUND OF THE INVENTION

Metal cations belonging to the first transition series are known to play important coenzymatic roles in metabolism. Zinc is known to be a coenzyme for over eighty different enzyme systems including those directly involved with DNA and RNA synthesis such as thymidine kinase, DNA and RNA polymerases, reverse transcriptase and terminal deoxynucleotide transferase. Among its other coenzyme functions, iron is the coenzyme for myoglobin, the cytochromes and catalases and is thus essential for oxidative metabolism. Manganese and copper also play significant coenzyme roles, and other metal cations in the first transition series are considered to be essential trace elements although their metabolic role is less well defined.

Compounds capable of forming complexes with metal cations, which compounds are commonly referred to as chelators or ligands, are known to have a variety of uses in medicine. These include their use as pharmaceuticals in treating heavy metal poisoning, in treating diseases associated with trace metal excess such as iron storage and copper storage diseases (hemosiderosis and Wilson's disease, respectively), as radiopharmaceutical agents in nuclear medical imaging when forming complexes with radioactive metals, as contrast enhancement agents in magnetic resonance imaging (MRI) when forming complexes with paramagnetic metals, and as contrast enhancement agents in radiography when forming complexes with heavy metals.

Examples of ligands employed in treating heavy metal poisoning such as that due to lead, mercury, and other metals, are ethylenediamine tetraacetic acid (EDTA) and diethylenetriamine pentaacetic acid (DTPA). The ligand desferrioxamine is used in treating iron storage disease, and the ligand penicillamine is used in the mobilization of copper in the treatment of Wilson's disease.

Examples of complexes used to form radiopharmaceuticals useful in evaluations of the kidneys, bone and liver are complexes of technetium-99m ($^{99m}Tc$) with diethylenetriamine pentaacetic acid (DTPA), dimercaptosuccinic acid (DMSA), methylene diphosphonate (MDP) and derivatives of iminodiacetic acid (IDA).

Complexes of paramagnetic metal cations which are useful as MRI contrast agents operate by accelerating proton relaxation rates. Most commonly a metal cation, such as gadolinium (III), having a large number of unpaired electrons is complexed by a ligand suitable for complexation of that cation. An example is gadolinium (III) complexed by DTPA.

Chelators with affinity for iron cations have been shown to inhibit cell proliferation. Desferrioxamine is one example of such a chelator. This effect is thought to be a consequence of the complexation of tissue iron by the chelator, which thereby deprives the proliferating cells of a source of iron for critical enzyme synthesis. Moreover, it is believed that certain types of tissue damage are mediated by the formation of free radicals. It is also appreciated that catalytically active iron catalyzes formation of the highly active hydroxyl free radical. Based on such relationships chelators (ligands) for iron such as desferrioxamine and the experimental iron chelator "L1" (1,2-dimethyl-3-hydroxypyrid-4-one) have been examined in management of conditions where free radical mediated tissue damage is believed to play a role, as well as in clinical management of conditions in which control of cell proliferation is desired. Conditions where the administration of iron chelators has been evaluated include: rheumatoid arthritis, anthracycline cardiac poisoning, reperfusion injury, solid tumors, hematologic cancers, malaria, renal failure, Alzheimer's disease, myelofibrosis, multiple sclerosis, drug-induced lung injury, graft versus host disease, and transplant rejection and preservation (Voest, E. E., et al., "Iron Chelating Agents in Non-Iron Overload conditions," *Annals of Internal Medicine* 120(6): 490–499 (Mar. 15, 1994)).

Agents which inhibit cell replication have found use in the prior art as chemotherapeutic agents for treatment of neoplasia and infectious disease, for suppression of the immune response, and for termination of pregnancy. Such agents usually act by inhibiting DNA, RNA or protein synthesis. This results in a greater adverse effect on rapidly proliferating cell populations than on cells "resting" in interphase or proliferating less rapidly.

Such agents may possess a degree of selectivity in treating the rapidly proliferating offending cell population, particularly in the case of certain neoplasias and infectious processes. These agents also inhibit replication of normal cells of the host organism, to varying degrees. Cells of the immune system proliferating in response to antigenic challenge are sensitive to such agents, and accordingly these agents are useful in suppressing the immunological response. Examples are the suppression of the homograft rejection response following tissue transplantation and the treatment of autoimmune disorders. Replication of protozoan, bacterial and mycotic microorganisms are also sensitive to such agents, which makes the agents useful in treating infections by such microorganisms.

Agents which suppress cell replication by inhibiting DNA or RNA synthesis have primarily found utility in treatment of neoplastic diseases. The glutamine antagonists azaserine, DON, and the anti-purines such as 6-mercaptopurine and 6-thioguanine principally inhibit DNA synthesis by their action on phosphoribosylpyrophosphate amidotransferase, the enzyme involved in the first step in purine nucleotide synthesis. The folic acid antagonists aminopterin arid methotrexate inhibit DNA synthesis (and other synthetic processes involving one carbon transport) by inhibiting the dihydrofolate reductase enzyme system, thereby interfering with formation of tetrahydrofolate, which is necessary in transfer of one-carbon fragments to purine and pyrimidine rings. Hydroxyurea inhibits DNA synthesis by inhibiting ribonuclease reductase, thereby preventing reduction of ribonucleotides to their corresponding deoxyribonucleotides. The anti-pyrimidines such as 5-fluorouracil inhibit DNA synthesis by inhibiting thymidylate synthetase. 5-Fluorouracil may also be incorporated into fraudulent RNA molecules. Bleomycin appears to inhibit DNA synthesis by blocking thymidine incorporation into DNA, although it may have other mechanisms of action. Agents such as 5-bromouracil and iododeoxyuridine may be incorporated into DNA in place of thymidine, and cytosine arabinoside may be incorporated into DNA in place of 2'-deoxycytidine. The fraudulent DNA produced by these incorporations interferes with the information transmittal system for DNA→RNA→protein synthesis.

Alkylating agents used in treating neoplasias, such as the nitrogen mustards, ethylene imines, alkyl sulphonates and antibiotics such as mitomycin C, suppress cell replication by attacking DNA and forming covalent alkylate linkages within preformed DNA, thereby interfering with DNA function and replication. The activity of such agents is therefore not limited to inhibition of cell replication alone.

Agents used in treatment of neoplasias such as 8-azaguanidine and 5-fluorouracil inhibit cell replication by being incorporated into fraudulent RNA. Agents such as actinomycin D, daunorubicin, nogalomycin, mithramycin and adriamycin are thought to inhibit RNA polymerase by strongly binding to DNA and thereby inhibiting DNA to RNA transcription.

Certain agents which inhibit cell replication by arresting metaphase (examples of such agents are colchicine, vinblastine, vincristine, podophyllotoxin, and griseofulvin) or arresting telophase (cytochalasins) have also been shown to be active in treating neoplasias or microbial infections.

Agents which inhibit cell replication primarily by inhibition of protein synthesis have found utility in the treatment of microbial infections. The tetracyclines, streptomycins and neomycin, for example, inhibit protein synthesis by inhibition of the mRNA-ribosome-tRNA complex. Chloramphenicol, erythromycin, lincomycin, puromycin appear to inhibit protein synthesis by inhibition of the peptidyl synthetase reaction. A miscellaneous group of antibiotics appear to act by inhibition of translocation of the ribosome along mRNA. Penicillins act by inhibiting synthesis of the bacterial cell wall.

Complexes of heavy metals such as platinum have been found to be active in treatment of certain neoplasias. The inhibition of cell replication by these complexes is attributed to the in vivo hydrolysis of one or more of the coordinating ligand sites occupying positions in the coordination shell of the metal. This hydrolysis liberates the coordination sites for in vivo interaction with nucleophilic donor sites which are critical to replication or survival of the cell population. There is a wide diversity of such donor sites in vivo, but it is believed that one critical set of donor sites involves binding of the platinum to two guanine or one guanine and one adenine residue of opposing strands of DNA.

The mechanisms of action of the various agents employed in treating protozoan infection are largely unknown. However, it has been demonstrated that agents which interfere with cell replication can be active in treating such infections. For example, the antimalarial agent chloroguanide and the diaminopyrimidines act as selective inhibitors of plasmodial dihydrofolate reductase thereby inhibiting plasmodial DNA replication. Tetracyclines possess antimalarial and antiprotozoal activities possibly acting by mechanisms similar to those operative in their inhibition of bacterial replication. The antibiotics puromycin and erythromycin, as well as tetracyclines which inhibit microbial replication, have also been employed in treatment of amebiasis. The antiprotozoal effects of the diamidines is believed to be due to their inhibition of cell replication by interference with DNA.

Based on what is known from the action of the agents cited above, one can readily conclude that agents which inhibit cell replication, regardless of the specific biochemical mechanism involved, have utility in the treatment of a wide variety of neoplastic and infectious diseases and in the management of certain of the body's responses which are mediated through selective in vivo cell replication.

SUMMARY OF THE INVENTION

The present invention resides in the discovery that a class of substituted polyaza compounds showing affinity and selectivity for first transition series elements (atomic numbers 21–30) are capable of inhibiting cell proliferation of mammalian, bacterial and yeast (fungal) cell populations and are therefore useful in vitro as preservatives and in vivo, administered topically or parenterally, in treatment of a wide variety of conditions including neoplasia, infection, inflammation, wound care, suppression of the immune response, inhibition of osteoclasts in treatment of osteoporosis and in termination of pregnancy. It is believed that the mechanism for inhibition of cell proliferation by these compounds lies in their ability to decrease the bioavailability of essential first transition series elements. The term "decrease the bioavailability" is used herein to denote a reduction or elimination of the accessibility of these elements to biological systems and thereby a reduction or elimination of the ability of these elements to perform the functions they would otherwise perform in living systems. Since these compounds decrease the bioavailability of zinc and iron, they are useful in inhibiting replication of DNA and RNA viruses. Since these compounds decrease the in vivo availability of tissue iron, they are also useful in management of free radical-mediated tissue damage and oxidation-mediated tissue damage. The compounds can also be prepared as complexes with radioisotopic or paramagnetic cations of first transition series elements, or with elements having chemical properties similar to those of first transition series elements. Complexes prepared in this manner are useful as diagnostic agents in nuclear medicine and magnetic resonance imaging.

By virtue of their affinity and selectivity, these substituted polyaza compounds are effective in treating diseases characterized by excess of first transition series elements, such as hemosiderosis (iron) and Wilson's disease (copper).

For therapeutic purposes these agents may be employed in their free ligand form or in a protected form (for example, as the ester of the pendant donor, group) where the protecting group can be removed in vivo by enzymatic action to release the active ligand form. The agents can be administered as either the free chelator, as a protected form of the chelator, or as physiological salts of these forms. Physiologically and pharmacologically acceptable salts of these compounds dissolved in suitable vehicles are fully suitable for use as pharmaceutical agents.

These compounds of this invention are chemically distinct from previously known antibiotic and chemotherapeutic agents which affect cell proliferation and which might also possess some properties as metal ion ligands. Unlike the chemotherapeutic complexes between a ligand and a heavy metal cation (such as platinum, for example) in which the complexed heavy metal provides the basis for the therapeutic effect and the purpose of the ligand portion of the complex is related to the in vivo distribution and hydrolysis rates of the complex, the compounds of this invention are active in the form of the metal-free ligand and do not require the addition of a heavy metal to exercise their therapeutic effect. The compounds of the invention are also chemically distinct from agents previously employed clinically as chelators of certain first transition series elements (such as desferrioxamine and 1,2-dimethyl-3-hydroxypyrid-4-one for chelation of iron, and penicillamine for chelation of copper).

Subclasses of compounds of this invention are novel compounds, structurally distinct from previously disclosed chelators and any complexes derived therefrom. Complexes of these subclasses in combination with radioisotopes or paramagnetic cations are particularly useful in diagnostic studies in nuclear medicine or in magnetic resonance imaging, respectively.

DETAILED DESCRIPTION OF THE INVENTION

Abbreviations

Abbreviations are used herein, in conformance with standard chemical practice, as follows: Bz, benzyl; Me, methyl; Et, ethyl; Pr, propyl; $^i$Pr, isopropyl; $^i$Bu, isobutyl; Bu, butyl; $^t$Bu, tertiary-butyl; Ts, para-toluenesulfonyl; Tf$^-$, trifluoroacetate; DMSO, dimethylsulfoxide; DMF, dimethylformamide; DEK, diethyl ketone (3-pentanone); MeOH, methanol; LDA, lithium diisopropylamide; THF, tetrahydrofuran; Py, pyridine; Ac, acetyl; Ac$_2$O, acetic anhydride

EMBODIMENTS OF THE INVENTION

The present invention provides methods of in vitro and in vivo complexing of first transition series element cations. The invention further provides methods of treating conditions dependent on the bioavailability of first transition series elements and also conditions associated with elevated levels of first transition series elements. Diagnostic methods are also provided which are useful in nuclear medicine and magnetic resonance imaging. The in vivo methods involve administering to a patient or host, a chelating agent (or ligand) which is capable of complexing first transition series elements as well as elements with chemical characteristics similar to those of first transition series elements. For the diagnostic methods, the chelating agent is administered as a complex of radioisotopic or paramagnetic cations of first transition series elements (or those with similar properties).

Among the ligands used in the practice of the present invention are the embodiments represented by the following formulas:

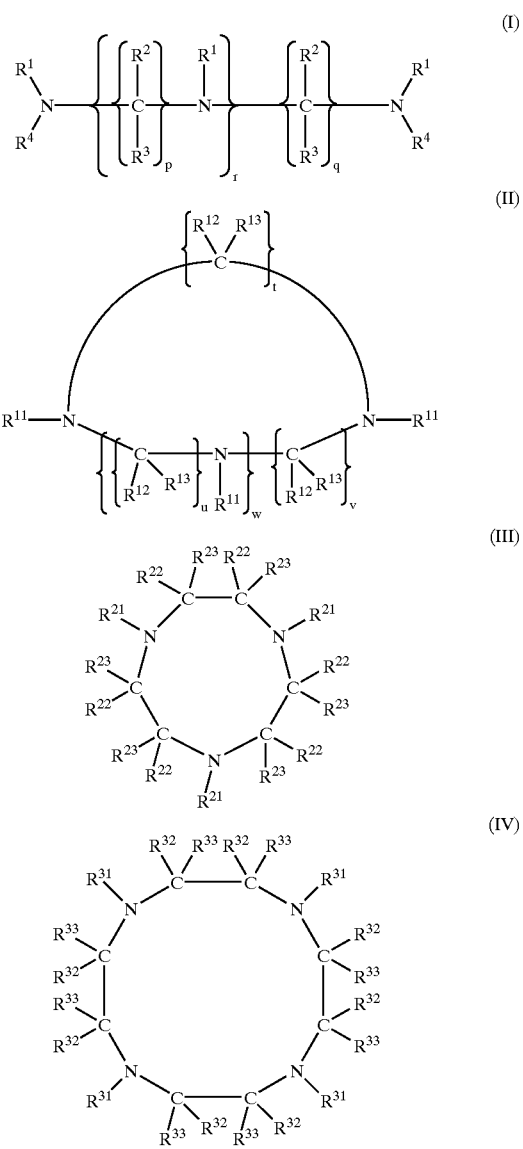

In Formulas I through IV, $R^1$, $R^2$, $R^3$, and $R^4$ may be the same or different on any single molecule, and the same is true for $R^{11}$, $R^{12}$, and $R^{13}$, for $R^{21}$, $R^{22}$, and $R^{23}$, and for $R^{31}$, $R^{32}$, and $R^{33}$. Each of these symbols ($R^1$ through $R^{33}$) represents H, alkyl, alkenyl, aryl, arylalkyl, alkoxy, alkylthio, alkenoxy, alkenylthio, aryloxy, arylthio, alkyl interrupted by one or more oxa (—O—), alkenyl interrupted by one or more oxa (—O—), alkyl interrupted by thia (—S—), alkenyl interrupted by thia (—S—), aryloxyalkyl, alkoxyaryl, aminoalkyl, aminoalkenyl, aminoaryl, aminoarylalkyl, hydroxyalkyl, hydroxyalkenyl, hydroxyaryl, or hydroxyarylalkyl, provided only that these groups do not interfere with complexation and they are not combined in a manner which results in a chemically unstable configuration. The alkyl, alkenyl and aryl groups, or portions of groups, in the foregoing list can also be substituted with one or more halogen atoms.

In addition to the radicals and radical subclasses listed above, $R^1$, $R^4$, $R^{11}$, $R^{21}$ and $R^{31}$ are further defined to include:

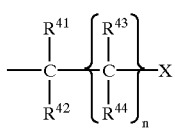
(V)

In Formula V, $R^{41}$, $R^{42}$, and $R^{43}$ may be the same or different on any single radical, and are defined as H, alkyl, alkenyl, aryl, arylalkyl, alkoxy, alkylthio, alkenoxy, alkenylthio, aryloxy, arylthio, alkyl interrupted by oxa (—O—), alkenyl interrupted by oxa (—O—), alkyl interrupted by thia (—S—), alkenyl interrupted by thia (—S—), aryloxyalkyl, alkoxyaryl, aminoalkyl, aminoalkenyl, aminoaryl, aminoarylalkyl, hydroxyalkyl, hydroxyalkenyl, hydroxyaryl, or hydroxyarylalkyl, provided only that these groups do not interfere with complexation and that they are not combined in a manner which results in a chemically unstable configuration. Here as well, the alkyl, alkenyl and aryl groups, or portions of groups, in the list can be substituted with one or more halogen atoms. $R^{44}$ in Formula V is defined as H, hydroxy, amino, alkyl, alkyl interrupted by oxa (—O—), alkoxy, aryl, aryloxyalkyl, alkoxyaryl, or any of these groups in which the alkyl and aryl portions are substituted with one or more halogen atoms. Again, the groups are selected such that they do not interfere with complexation and are not combined in a manner which results in a chemically unstable configuration.

The index n is either zero or 1.

The symbol X represents any of the following groups:

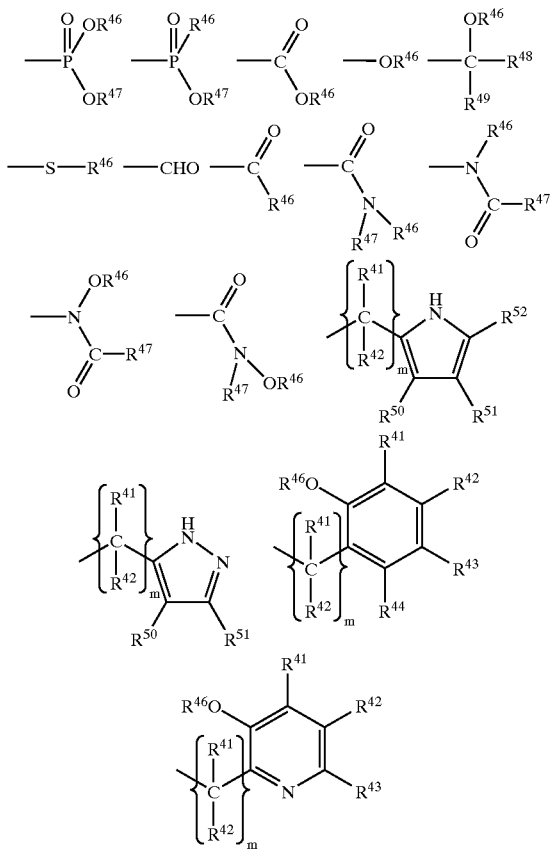

In these formulas, $R^{41}$, $R^{42}$, $R^{43}$, and $R^{44}$ may be the same or different on any single radical, and have the same definitions as $R^{41}$, $R^{42}$, and $R^{43}$ given above.

$R^{46}$, $R^{47}$, $R^{48}$ and $R^{49}$ may be the same or different on any single radical, and are each defined as H, or alkyl or aryl groups which do not interfere with complexation. $R^{46}$ and $R^{47}$ may further be combined as a single divalent group, thereby forming a ring structure. $R^{48}$ and $R^{49}$ are further defined to include alkoxy, alkyl interrupted by oxa (—O—), aryloxyalkyl, and alkoxyaryl, combined in a manner which results in a chemically stable configuration. All alkyl and aryl groups in this paragraph, including alkyl and aryl portions of groups, are optionally substituted with one or more halogen atoms.

$R^{50}$, $R^{51}$ and $R^{52}$ may be the same or different on any single radical, and are each defined as H, alkyl, alkenyl, aryl, arylalkyl, alkyloxy, alkylthio, alkenyloxy, alkenylthio, aryloxy, arylthio, aminoalkyl, aminoalkenyl, aminoaryl, aminoarylalkyl, hydroxyalkyl, hydroxyalkenyl, hydroxyaryl, or hydroxyarylalkyl.

The index m is an integer which is either 1, 2 or 3.

Returning to Formulas I through IV, further variations within the scope of this invention are as follows:

(1) Internal cyclizations within these formulas at the nitrogen atoms, formed by joining together any two of the $R^1$ and $R^2$ groups in Formula I, any two of the $R^{11}$ groups in Formula II, any two of the $R^{21}$ groups in Formula III, or any two of the $R^{31}$ groups in Formula IV, as a single divalent group bridging the two nitrogen atoms, the single divalent group having the formula $$\left[\begin{array}{c} R^2 \\ | \\ -C- \\ | \\ R^3 \end{array}\right]_s$$
(VI)

in which $R^2$ and $R^3$ are as defined above, and s is at least 2, preferably 2 or 3;

(2) Dimers or other two-molecule combinations of Formulas I through IV (the molecules being the same or different), formed by bridging the molecules together through one or more divalent groups of Formula VI (as defined above) substituted for any one or two of the $R^{11}$ groups in Formula II, any one or two of the $R^{21}$ groups in Formula III, or any one or two of the $R^{31}$ groups in Formula IV;

(3) Internal cyclizations at common carbon atoms within these formulas to form homocyclic rings, by joining one or more of the $R^2$, $R^{12}$, $R^{22}$, or $R^{32}$ groups to one or more of the $R^3$, $R^{13}$, $R^{23}$, or $R^{33}$ groups at the same carbon atom, as a single divalent group of Formula VI (as defined above), and forming one or more such homocyclic rings per structure in this manner; and (4) Internal cyclizations involving two carbon atoms separated by a nitrogen atom within these formulas to form heterocyclic rings, by joining any two adjacent $R^2$ groups in Formula I, any two adjacent $R^{12}$ groups in Formula II, any two adjacent $R^{22}$ groups in Formula III, or any two adjacent $R^{32}$ groups in Formula IV, as a single divalent group of Formula VI (as defined above), and forming one or more such heterocyclic rings per structure in this manner.

In Formula I, the subscripts p and q may be the same or different, and are each either 2 or 3. The subscript r is 0 to 4 inclusive, preferably 1 to 2 inclusive.

In Formula II, t, u and v may be the same or different, and are each either 2 or 3. The value of w is at least 1, more preferably 1 to 4 inclusive, still more preferably 1 to 3 inclusive, and most preferably either 1 or 2.

The terms used in connection with these formulas have the same meaning here as they have in the chemical industry among those skilled in the art. The term "alkyl" thus encompasses both straight-chain and branched-chain groups and includes both linear and cyclic groups. The term "alkenyl" refers to unsaturated groups with one or more double bonds and includes both linear and cyclic groups. The term "aryl" refers to aromatic groups of one or more cycles.

For all such groups, those which are useful in the present invention are those which do not impair or interfere with the formation of chelate complexes. Within this limitation, however, the groups may vary widely in size and configuration. Preferred alkyl groups are those having 1 to 8 carbon atoms, with 1 to 4 carbon atoms more preferred. Prime examples are methyl, ethyl, isopropyl, n-butyl and tert-butyl. Preferred aryl groups are phenyl and naphthyl, particularly phenyl. Preferred aryl alkyl groups are phenylethyl and benzyl, and of these benzyl is the most preferred. Preferred cycloalkyl groups are those with 4 to 7 carbon atoms in the cycle, with cycles of 5 or 6 carbon atoms particularly preferred. Preferred halogen atoms are chlorine and fluorine, with fluorine particularly preferred.

One particularly preferred subclass of compounds within Formula I are those in which $R^1$ is alkyl, alkenyl, aryl, arylalkyl, or cycloalkyl, substituted at the β-position with hydroxy. Likewise, $R^{11}$ in Formula II, $R^{21}$ in Formula III, and $R^{31}$ in Formula IV are each preferably alkyl, alkenyl, aryl, arylalkyl, or cycloalkyl, substituted at the β-position with hydroxy. Further preferred are compounds in which one or more, and preferably two or more, of such groups ($R^1$, $R^{11}$, $R^{21}$ and $R^{31}$ on the same formula are substituted at the β-position with hydroxy. Still further preferred are compounds in which the β-hydroxy substituted groups are further substituted at the β-position with at least one hydroxymethyl, alkoxymethyl, alkenoxymethyl, aryloxymethyl, or combinations thereof, all of which may also be further substituted with halogen. Included among these are compounds are compounds of Formula III in which one or more of the $R^{21}$ groups are substituted at the β-position with hydroxy and also with hydroxymethyl, alkoxymethyl, alkenoxymethyl, or aryloxymethyl, all of which may also be further substituted with halogen, and the $R^{22}$ and $R^{23}$ groups are all hydrogen atoms.

Certain specific groups for $R^1$, $R^{11}$, $R^{21}$, and $R^{31}$ are particularly preferred. These are: 2-hydroxy(2,2-diisopropoxymethyl)ethyl and (3-hydroxy-6,6,7,7-tetramethyl-1,5-dioxacyclohept-3-yl)methyl.

For use in the present inventive methods, the complexes will preferably have a molecular weight which does not exceed 2000. More preferably the complexes will have molecular weights of from 200 to 1800, still more preferably of from 400 to 1100.

Among the complexes used in the practice of the present invention are the embodiments represented by the complexes formed between the ligands described above and paramagnetic metal cations or radioisotopic metal cations. These paramagnetic metal cations include elements of atomic numbers 22 through 29 (inclusive), 42, 44 and 58 through 70 (inclusive). Of these, the ones having atomic numbers 22 through 29 (inclusive) and 58 through 70 (inclusive) are preferred, and those having atomic numbers 24 through 29 (inclusive) and 64 through 68 (inclusive) are most preferred. Examples of such metals are chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III). Chromium (III), manganese (II), iron (III) and gadolinium (III) are particularly preferred, with gadolinium (III) the most preferred.

Some methods of the present invention will use radioisotopic labels which will facilitate imaging of various disease states including tumors, inflamed joints or lesions or suspected lesions. The use of gamma emitting radioisotopes is particularly advantageous as they can easily be counted in a scintillation well counter, do not require tissue homogenization prior to counting, and can be imaged with gamma cameras.

Gamma or positron emitting radioisotopes are typically used in accordance with well known techniques. Suitable gamma-emitting radioisotopes include $^{99}$Tc, $^{51}$Cr, $^{59}$Fe, $^{67}$Ga, $^{86}$Rb, $^{111}$In and $^{195}$Pt. Suitable positron-emitters include $^{68}$Ga.

Where indicated, physiologically or pharmacologically compatible salts of the ligands, or complexes thereof, which have an excess of acidic groups are formed by neutralizing the acidic moieties of the ligand with physiologically or pharmacologically compatible cations from corresponding inorganic and organic bases and amino acids. Examples are alkali and alkaline earth metal cations, notably sodium. Further examples are primary, secondary and tertiary amines, notably, ethanolamine, diethanolamine, morpholine, glucamine, N,N-dimethylglucamine, and N-methylglucamine (commonly referred to as "meglumine"). Examples of amino acid cations are lysines, arginines and ornithines.

Similarly, physiologically and pharmacologically compatible salts of those ligands which have an excess of basic groups are formed by neutralizing the basic moieties of the ligand with physiologically or pharmacologically compatible anions from corresponding inorganic and organic acids. Examples are halide anions, notably chloride. Further examples are sulfates, bicarbonate, acetate, pyruvate and other inorganic and organic acids.

Pharmaceutical compositions comprising the chelates described herein are prepared and administered according to standard techniques. The pharmaceutical compositions can be administered parenterally, i.e., intraarticularly, intravenously, subcutaneously, or intramuscularly. Suitable formulations for use in the present invention are found in *Remington's Pharmaceutical Sciences*, Mack Publishing Company, Philadelphia, Pa., 17th ed. (1985).

The chelate compositions can be administered intravenously. Thus, this invention provides compositions for intravenous administration which comprise a solution of the chelate suspended in an acceptable carrier, preferably an aqueous carrier. A variety of aqueous carriers may be used, e.g., water, buffered water, 0.9% isotonic saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, calcium chloride, sorbitan monolaurate, triethanolamine oleate, etc.

The concentration of chelates, in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For diagnosis, the amount of chelates in administered complexes will depend upon the particular metal cation being used and the judgement of the clinician. For use in magnetic resonance imaging the dose typically is between 0.05 to 0.5 millimoles/kg body weight.

In general, any conventional method for visualizing diagnostic imaging can be used, depending upon the label used. Usually gamma and positron emitting radioisotopes are used for imaging in nuclear medicine and paramagnetic metal cations are used in magnetic resonance imaging.

The methods of the present invention may be practiced in a variety of hosts. Preferred hosts include mammalian species, such as humans, non-human primates, dogs, cats, cattle, horses, sheep, and the like.

The foregoing description and the following examples are offered primarily for illustration and not as limitations. It will be readily apparent to those of ordinary skill in the art that the operating conditions, materials, procedural steps and other parameters of the compositions and methods described herein may be further modified or substituted in various ways without departing from the spirit and scope of the invention.

EXAMPLES

Example 1

This example illustrates the synthesis of chelators (ligands) which are useful in the present invention. Section 1.1 illustrates the synthesis of polyaza bases. Section 1.2 illustrates the synthesis of alkylating groups. Section 1.3 illustrates the preparation of chelating agents from alkylation of polyaza bases.

In all examples reactions were carried out in common solvents, compounds were purified by routine methodology and identity was established by proton NMR. In some cases identity was further verified by elemental analysis, mass spectroscopy, C-13 or P-31 NMR, or by synthesis of the identical compound by an independent alternate synthesis route.

1.1 Synthesis of Polyaza Bases

Ethylene diamine (1.1.0), diethylene triamine (1.1.1), triethylenetetramine (1.1.2), 1,4,7-triazacyclononane (1.1.3), 1,4,7,10-tetraazacyclododecane (1.1.4), 1,4,8,11-tetraazacyclotetradecane (1.1.5) & 1,5,9,13-tetraazacyclohexadecane (1.1.6) and the corresponding hydrohalide salts were either obtained from commercial sources or were synthesized employing established methods and were used directly in the syntheses of chelators (ligands) described in section 1.3. Additional polyaza bases were synthesized as described herein.

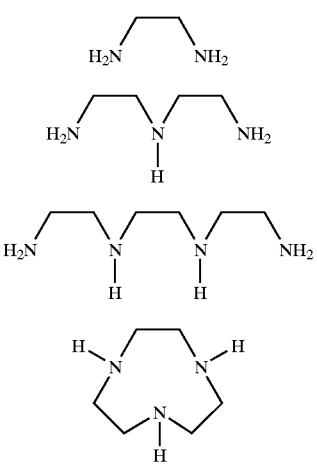

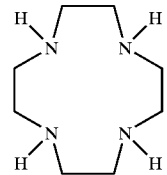

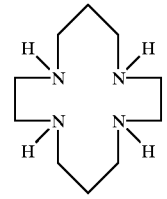

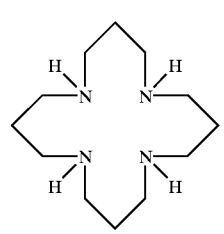

1.1.7 2,6-Diethyl-1,4,7-triazacyclononane trihydrobromide 2-(p-toluenesulfonylamino)-1-(p-toluenesulfonyloxy)butane (1.1.8) and ammonium hydroxide were reacted to form 2-(p-toluenesulfonamino)-1-aminobutane (1.1.9). This was reacted with 2-(p-toluenesulfonylamino)-1-(p-toluenesulfonyloxy) butane (1.1.8) and potassium carbonate. The 3,7 bis(p-toluenesulfonylamino)-5-azanonane (1.1.10) product was purified by chromatography and reacted with p-toluenesulfonyl chloride to obtain the corresponding tri-p-toluenesulfonyl compound 3,7 bis(p-toluenesulfonylamino)-5-(p-toluenesulfonyl-5-azanonane (1.1.11). This was purified by chromatography and reacted with 2.2 equivalents of sodium amide in DMF and then with 1,2-di(p-toluenesulfonyloxy)ethane (1.1.12). The 2,6-diethyl-1,4,7-tris (p-toluenesulfonyl)triazacyclononane (1.1.13) that was obtained following purification was heated in a solution of HBr in acetic acid to remove the p-toluenesulfonyl groups and form the titled compound (1.1.7)

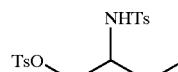

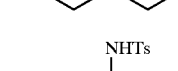

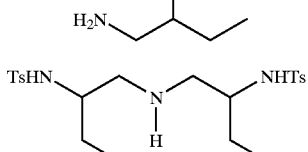

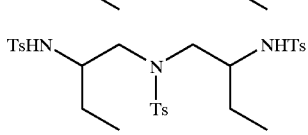

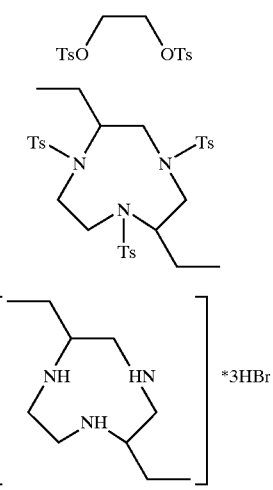

1.1.14 1,4,7-Triazabicyclo[7.4.0$^{8,13}$]tridecane trihydrobromide 1,2-trans-bis(p-toluenesulfonylamino)cyclohexane (1.1.15) was treated with NaH in DMSO. 1-(p-toluenesulfonylamino)-2-(p-toluenesulfonyl)ethane (1.1.16) was added to obtain 1-(p-toluenesulfonylamino)-2-[N-p-toluenesulfonyl-N-(2-p-toluenesulfonylaminoethyl)] aminocyclohexane (1.1.17). This was separated and reacted with NaH and 1,2-di(p-toluenesuffonyloxy)ethane (1.1.12) was added. The 2,3-butano-N,N'N"-tris(p-toluenesulfonyl)-1,4,7-triazacyclononane (1.1.18) obtained was purified by chromatography. The p-toluenesulfonyl groups were removed by reaction in HBr/Acetic acid and the 2,3-butano-1,4,7-triazacyclononane trihydrobromide (1.1.14) product precipitated from solution as the hydrobromide salt.

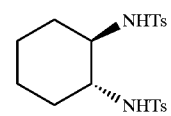

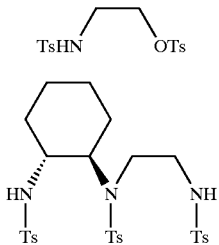

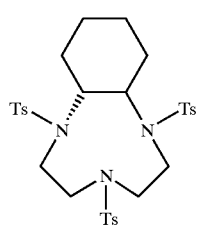

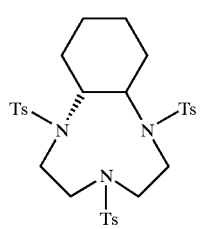

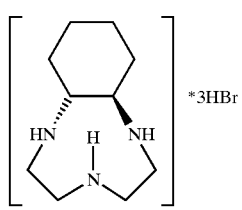

1.1.19 1,3-Bis (1,4,7-triazacyclononane)propane

N,N'-bis(p-toluenesulfonyl)-1,4,7-triazacyclononane (1.1.20) was prepared by reacting (1.1.3) with two equivalents of p-toluenesulfonyl chloride. Two equivalents of N,N'-bis(p-toluenesulfonyl)-1,4,7-triazacyclononane (1.1.20) hydrobromide were reacted with one equivalent of 1,3-diiodopropane in acetonitrile with excess potassium carbonate. 1,3-Bis[N,N'-bis(p-toluenesulfonyl)-1,4,7-triazacyclononane propane (1.1.21) was isolated and purified by chromatography. The p-toluenesulfonyl groups were removed using sulfuric acid and HBr to yield the title compound (1.1.19).

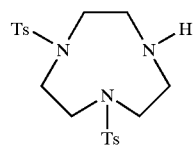

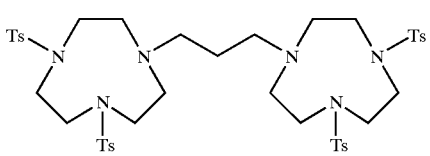

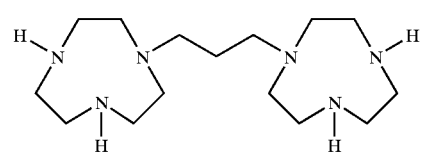

1.1.22 1,4,7,10-Tetraazabicyclo[5.5.2]tetradecane 1,4,7,10-tetraazadodecane (1.1.4) trihydrobromide in acetonitrile with potassium carbonate was reacted with glyoxal to form 1,4,7,10-tetraazatetracyclo-[5,5,2,0$^{4,13}$,0$^{10,14}$]tetradecane (1.1.23). Following separation the pure product was obtained by low pressure distillation. This was dissolved in acetonitrile and benzylbromide was added to form 1,7-dibenzylonium-1,4,7,10-tetraazatetracyclo[5,5,2,0$^{4,13}$,0$^{10,14}$]tetradecane (1.1.24). Following recrystallization from ethanol this was reacted with sodium borohydride. HCl was added, followed by water and NaOH, and the product extracted with chloroform. Following evaporation of solvent the solids were dissolved in methanol and HBr was added to obtain 1,7-dibenzyl-1,4,7,10-tetraazabicyclo [5.5.2] tetradecane (1.1.25) as the hydrobromide salt. This was dissolved in water and reduced using H$_2$ and a Pd—C catalyst to remove the benzyl groups. Purification of the title compound was by crystallization of the hydrobromide salt. The base form was obtained by low pressure distillation following addition of base.

1.1.23

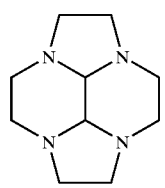

1.1.24

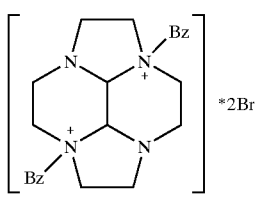

1.1.25

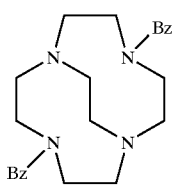

1.1.22

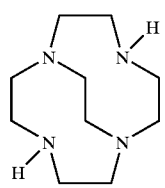

1.1.26 1,4,7,10,13-Pentaazabicyclo[8.5.2] heptadecane

To 1,8-bis(p-toluenesulfonyloxy)-3,6-bis(p-toluenesulfonyl)-3,6-diazaoctane(1.1.27) was added 1,4,7-triazacyclononane(1.1.3) in acetonitrile with potassium bicarbonate to obtain 4,7-bis(p-toluenesulfonyl)-1,4,7,10,13-pentaazabicyclo[8.5.21 (1.1.28) heptadecane. The title compound was purified and the p-toluenesulfonyl groups were removed by treatment in sulfuric acid. Purification was done by low pressure distillation.

1.1.27

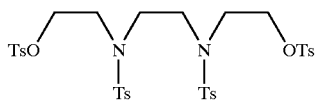

1.2.28

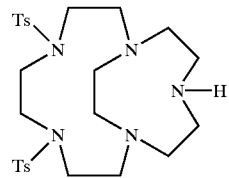

1.2.26

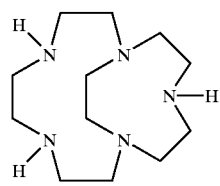

1.1.29 1,2-Bis(1,4,7-triazabicyclononane-1-yl) ethane

A mixture of N, N'-bis(p-toluenesulfonyl)-1,4,7-triazabicyclonone hydrobromide (1.1.13.33), ethylene glycol di-p-toluenesulfonyl or dibromoethane and excess of potassium carbonate in acetonitrile was refluxed overnight. The reaction mixture was added to water and extracted with methylene chloride. The tetratosylated product (1.1.30) was purified by chromatography. It was suspended in 70% $H_2SO_4$ and heated at 150° C. for 15 hrs. The reactions cooled to room temperature and then 62% HBr solution was added. The white precipitate was collected and washed with ethanol. It was redissolved in water and filtered from tars. The water was made basic and the title compound (1.1.29) was extracted with chloroform.

1.1.30

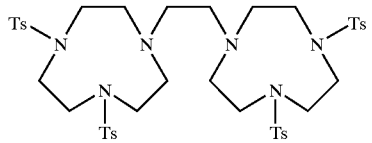

1.1.29

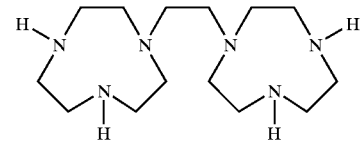

1.2 Synthesis of Alkylating Groups for Alkylation of Polyaza Bases to Form Chelators Described in Example 1.3.

1.2.1 Preparation of Glycidyl Ethers

Glycidyl tosylate (R,S or d,l) (1.2.1.0) was reacted in the appropriate alcohol solvent employing catalytic amounts of conc. $H_2SO_4$ or equivalent amounts of tetrafluoroboranetherate. The 1-alkyloxy-2-hydroxy-3-p-toluenesulfonyloxypropane (1.2.1.1) product was reacted in ether with BuLi to yield the title epoxide. The following compounds were prepared in this manner.

1.2.1.0 Glycidyl tosylate (R,S or d,l; Commercially Available)

1.2.1.0

1.2.1.1 1-Alkyloxy-2-hydroxy-3-P-toluenesulfonyloxypropane 1.2.1.1

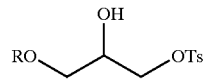

1.2.1.2 d,l-Glycidyl-isopropyl ether (Commercially Available)

1.2.1.2

1.2.1.3 (2R) Glycidyl-isopropyl ether

1.2.1.4 (2S) Glycidyl-isopropyl ether

1.2.1.5 d,l-Glycidyl-t-butyl ether

1.2.1.5

1.2.1.6 (2R) Glycidyl-t-butyl ether

1.2.1.7 d,l-Glycidyl allyl ether

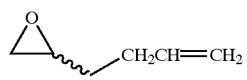

1.2.1.7

1.2.1.8 d,l-Glycidyl phenyl ether

1.2.1.8

1.2.2 Preparation of 2,2-Dialkoxymethylene Oxiranes and Spiro-Oxiranes

3-Chloro-2-chloromethyl-1-propane (1.2.2.0) was reacted with the corresponding sodium alkylate or disodium dialkylate either using the same alcohol or dialcohol as solvent or using an inert solvent. The ether product was purified by distillation or chromatography. Epoxidation was performed using meta-chloroperbenzoic acid in halogenated solvent. The following compounds were prepared in this manner.

1.2.2.0 3-Chloro-2-chloromethyl-1-propane (Commercially Available)

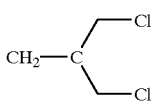

1.2.2.0

1.2.2.1. 2,2-Bis-ethoxymethyl oxirane

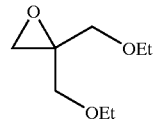

1.2.2.1

1.2.2.2 2,2-Bis-methoxymethyl oxirane

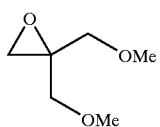

1.2.2.2

1.2.2.3 2,2-Bis-isopropyloxymethyl oxirane

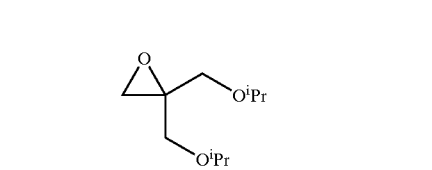

1.2.2.3

1.2.2.4 2,2-Bis-difurfuryloxymethyl oxirane

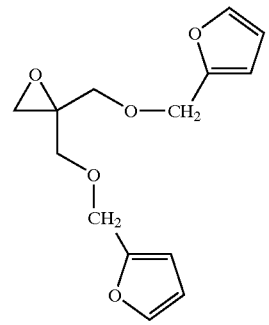

1.2.2.4

1.2.2.5 2,2-Bis(hydroxymethyl)oxirane

From 2-methylidene-1,3-dihydroxypropanediol (commercially available).

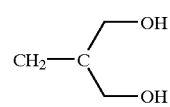

1.2.2.5

1.2.3 Preparation of Oxiranespiro-3-(1,5-Dioxacycloalkanes)

Various dry glycols in DMF were reacted with NaH and 3-chloromethyl-1-propane (1.2.2.0) was added to the resulting reaction mixture. Following completion of the reaction the solvents were removed and the product purified by low pressure distillation. The purified product in dichloroethane was reacted with m-chloroperbenzoic acid to form the corresponding epoxide. Following workup, the epoxide product was purified by distillation. The following compounds were prepared in this manner.

1.2.3.1 Oxiranespiro-3-(1,5-dioxacycloheptane)

(From ethylene glycol)

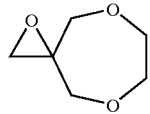

1.2.3.1

1.2.3.2 Oxiranespiro-3-(1,5-dioxa-7,7-dimethylcyclooctane)

(From 2,2-dimethyl propylene glycol)

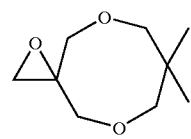

1.2.3.2

1.2.3.3 Oxiranespiro-3-(1,5-dioxa-6-methylcycloheptane)

(From 1,2-dihydroxy propane)

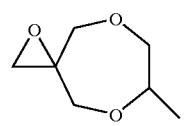

1.2.3.3

1.2.3.4 Oxiranespiro-3-(1,5-dioxa-6,6,7,7-tetramethylcycloheptane)

[From 2,3-dihydroxy-2,3-dimethyl butane (pinacol)].

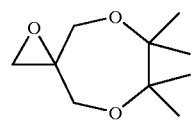

1.2.3.4

1.2.3.5 Oxiranespiro-3-(benzo[b]-1,5-dioxacycloheptane)

(From 1,2-dihydroxybenzene).

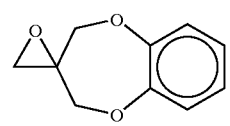

1.2.3.5

1.2.3.6 Oxiranespiro-3-(1,5-dioxacycloctane)

(From 1,3-propanediol)

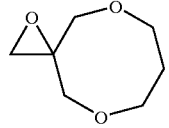

1.2.3.6

1.2.4 Preparation of Miscellaneous Epoxides

1.2.4.1 2,2-dimethyl oxirane (From 2-methyl-1-propene and m-chloroperbenzoic acid.

1.2.4.1

1.2.4.2 2-(Isopropyl)-2-[(1-fluoro-1-methyl)ethyl] oxirane

Reaction between 2,4-dimethyl-3-pentanone (1.2.4.3), trimethylsilyl chloride, and base gave 2,4-dimethyl-3-trimethysilyloxy-2-pentene (1.2.4.4) which was reacted with 1-fluoropyridinium triflate (1.2.4.5) to form 2,4-dimethyl-2-fluoro-3-pentanone (1.2.4.6). This product was reacted with $(CH_3)_3S(O)^+I^-$ to form the title compound (1.2.4.2).

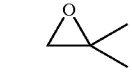

1.2.4.3

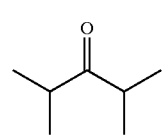

1.2.4.4

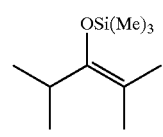

1.2.4.5

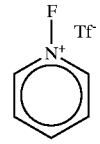

1.2.4.6

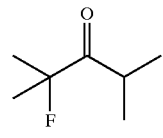

1.2.4.2

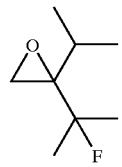

1.2.4.7 2,2-Bis-isopropyl oxirane (From 2,4-dimethylpentanone using $(CH_3)_3S(O)^+I^-$ as described in 1.2.4.2)

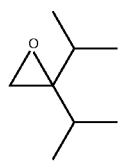

1.2.4.8 2-(1-Fluoroethyl)-2-(1-trimethylsilyloxyethyl)oxirane

The title compound was obtained in several steps. DEK was O-silylated using usual procedure. The resulting product was reacted with 1-fluoropyridinium triflate (1.2.4.5) to yield 2-fluoro-3-pentanone (1.2.4.9). After bromination the 2-bromo-4-fuoro-3-pentanone (1.2.4.10) which was obtained was reacted with liquid ammonia to form 2-fluoro-4-hydroxy-3-pentanone (1.2.4.11). The free hydroxyl group was protected with trimethylsilylchloride to form 2-fluoro-4-trimethylsilyloxo-3-pentanone (1.2.4.12). This product was reacted with trimethylsulfoxonium iodide to form the title compound (1.2.4.8).

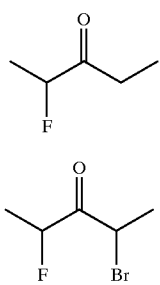

1.2.4.9

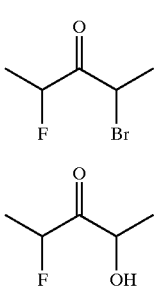

1.2.4.10

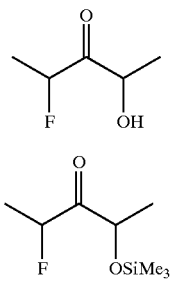

1.2.4.11

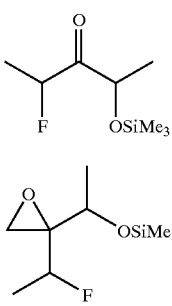

1.2.4.12

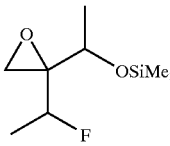

1.2.4.8

1.2.4.13 2-(1-Bromoethyl)-3-methyl oxirane

Bromination of diethyl ketone with bromine gave 2,4-dibromo-3-pentanone (1.2.4.14). This product was reduced with BH$_3$/THF to form 3-hydroxy-2,4-dibromopentane (1.2.4.15). After treatment with base the title compound (1.2.4.13) was obtained.

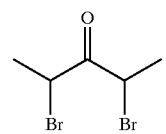

1.2.4.14

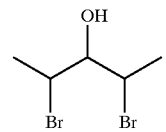

1.2.4.15

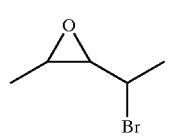

1.2.4.13

1.2.4.16 2-(1-Fluoroethyl)-3-methyl oxirane

From reaction between diethylketone and trimethyichlorosilane to form 3-trimethylsilyloxy-2-pentene (1.2.4.17). This product was reacted with 1-fluoropyridinium triflate (1.2.4.5) to obtain 2-fluoro-3-pentanone (1.2.4.9). After bromination with pyridinium bromide followed by reduction using diborane 2-fluoro-4-bromopentane-3-ol (1.2.4.18) was obtained. Reaction of this product with sodium methylate yielded the title compound (1.2.4.16). This compound was made also by reacting 2-(1-bromoethyl)-3-methyl oxirane (1.2.4.13) with HF/Py (70%) followed by treatment of the resulting 2-bromo-4-fluoropentan-3-ol (1.2.4.18) with K$_2$CO3/MeOH.

1.2.4.19 2-(1-Fluoroethyl)-2-(1-methoxyethyl) oxirane

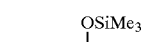

1.2.4.17

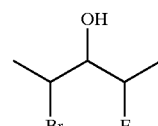

1.2.4.18

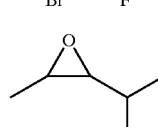

1.2.4.16

2-(1-Fluoroethyl)-3-methyl oxirane (1.2.4.16) was reacted with methanol/sulfuric acid to obtain 2-fluoro-4-methoxypentane-3-ol (1.2.4.20). This product was reacted with chromic anhydride/pyridine to form 2-fluoro-4-methoxypentane-3-one (1.2.4.21) which was then reacted with sodium hydride and trimethylsulfoxonium iodide to obtain the title compound (1.2.4.19).

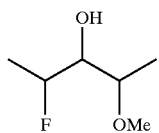

1.2.4.20

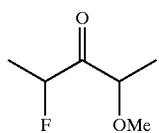

1.2.4.21

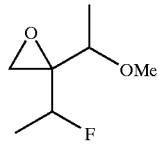

1.2.4.19

1.2.4.22 2-(1-Methoxyethyl)-3-methyl oxirane

Reaction of 2-(1-Bromoethyl)-3-methyl oxirane (1.2.4.13) with methanol/sulfuric acid formed 2-bromo-3-hydroxy-4-methoxypentane (1.2.4.23). This product was reacted with potassium carbonate in methanol to obtain the title compound (1.2.4.22).

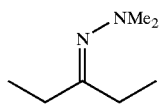

1.2.4.23

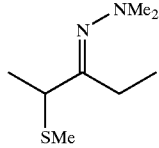

1.2.4.22

1.2.4.24 2-Ethyl-2-(1-methoxyethyl)oxirane

Reaction between diethyl ketone and dimethyl hydrazine gave diethyl ketone-N,N-dimethylhydrazone (1.2.4.25). This product was reacted with dimethyl disulfide/LDA to obtain 2-methylthio-3-pentanone-N,N-dimethyl hydrazone (1.2.4.26). This product was reacted with mercuric chloride followed by cupric chloride to obtain 2-methoxy pentane-3-one (1.2.4.27). Reaction of the latter compound with sodium hydride/DMSO/trimethylsulfonium iodide yielded the title compound (1.2.4.24).

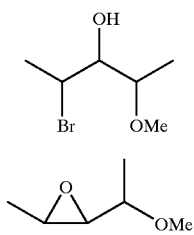

1.2.4.25

1.2.4.26

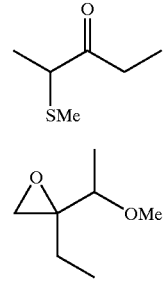

1.2.4.27

1.2.4.24

1.2.4.28 2-Ethyl-2-(1-trimethylsilyloxyethyl)oxirane

From reaction between 2-bromo-3-pentanone (1.2.4.29) and hydrazine obtained 2-hydroxy-3-pentanone (1.2.4.30). This product was reacted with trimethylchlorosilane/triethylamine to obtain 2-trimethylsilyloxy-3-pentanone (1.2.4.31). This product was reacted with methylenetriphenyl phosphite and butyllithium to obtain 2-ethyl-3-trimethylsilyloxy-1-butene (1.2.4.32). After oxidation with meta-chloroperbenzoic acid in methylene chloride the title compound (1.2.4.28) was obtained.

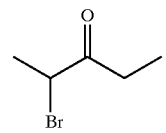

1.2.4.29

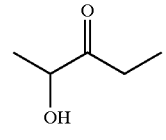

1.2.4.30

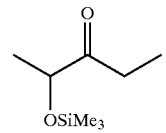

1.2.4.31

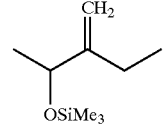

1.2.4.32

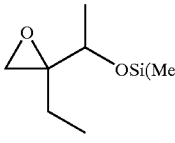

1.2.4.28

1.2.4.33 2,2-Bis(1-fluoroethyl)oxirane

From reaction between 2-(1-Bromoethyl)-3-methyl oxirane (1.2.4.13) and HF/pyridine was obtained 2-bromo-4-fluoro-pentane-3-ol (1.2.4.18). This was reacted with potassium carbonate to obtain 2-(1-fluoroethyl)-3-methyl oxirane (1.2.4.16). This was reacted again with HF/pyridine to obtain 2,4-difluoro-pentane-3-ol (1.2.4.34). After oxidation with chromium trioxide obtained 2,4-difluoro-3-pentanone (1.2.4.35). The epoxide title compound was prepared from the ketone as described for 1.2.4.24.

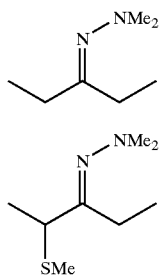

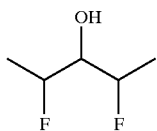

1.2.4.34

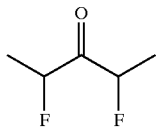

1.2.4.35

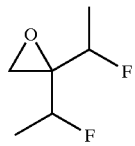

1.2.4.33

1.2.3.36 2,2-Bis-dichloromethyleneoxirane (From direct epoxidation of 3-chloro-2-chloromethyl-1-propene).

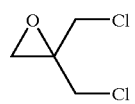

1.3.4.36

1.2.4.37 2,2-Bis(1-methoxyethyl)oxirane

3-Pentanone was brominated to get 2,4-dibromo-3-pentanone (1.2.4.11) using conventional methods. The dibromoketone was reduced with BH$_3$*THF to the corresponding alcohol (1.2.4.15). This compound was reacted with MeONa in methanol to yield 2-(1-bromoethyl)-3-methyl oxirane (1.2.4.13) which after reaction with MeOH/H$_2$SO$_4$ gave 2-bromo-3-hydroxy-4-methoxy pentane (1.2.4.38). This intermediate was reacted again with MeONa in methanol and the resulting 2-(1-methoxyethyl)-3-methyl oxirane (1.2.4.22) was reacted again with MeOH/H$_2$SO$_4$ to yield 2,4-dimethoxy-3-hydroxy pentane (1.2.4.39). After oxidation with CrO$_3$/Py in methylenechloride the resulting ketone was reacted with trimethylsulfoxonium iodide to give the title compound (1.2.4.37).

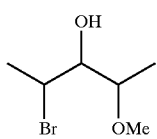

1.2.4.38

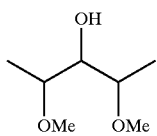

1.2.4.39

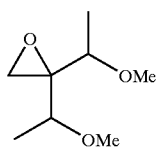

1.2.4.37

1.2.5 Phosphite and Alkyl Phosphonate Esters

Dialkylphosphites were prepared by reacting diethylphosphite with the corresponding alcohol.

1.2.5.1 Di-n-butylphosphite, HP(O)[OCH$_2$(CH$_2$)$_2$CH$_3$]$_2$ (From n-butyl alcohol)

1.2.5.2 Dioctylphosphite, HP(O)[OCH$_2$(CH$_2$)$_6$CH$_3$]$_2$ (From octyl alcohol)

1.2.5.3 Diisobutylphosphite, HP(O)(O$^i$Bu)$_2$ (From iso butyl alcohol)

1.2.5.4 Dibenzyl phosphite, HP(O)(OCH$_2$Ph)$_2$ (From benzyl alcohol).

1.2.5.5 Diethyl(2-bromoethyl) phosphonate, BrCH$_2$CH$_2$P(O)(OEt)$_2$ (From reaction between triethylphosphite and 1,2-dibromethane)

1.2.5.6 Diethyl(2-chloro-1-hydroxyethyl) phosphonate ClCH$_2$CH(OH)P(O)(OEt)$_2$ (From reaction of diphenylphosphite and chloroacetaldehyde).

1.2.5.7 2.(Diethylphosphonate)oxirane (From 1.2.5.6, sodium ethoxide).

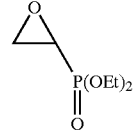

1.2.5.7

1.2.6 Halides and Tosylates 1.2.6.1 1-Bromo-2-hydroxy-3,3 dimethylbutane, BrCH$_2$CH(OH)C(CH$_3$)$_2$ (From reduction of bromomethyl-t-butyl ketone by BH3/THF).

1.2.6.2 1-Bromo-2-t-butyldimethylsilyloxyethane, BrCH$_2$CH$_2$Si($^t$Bu)(CH$_3$)$_2$ (From bromoethanol and dimethyl-t-butylsilylchloride)

1.2.6.3 5-(p-Toluenesulfonyloxymethylene)-1-benzyloxy-2-pyrrolidone

This compound was prepared in several steps. 4-pentenoic acid (1.2.6.4) was reacted with ethylchloroformate in the usual way to obtain the active mixed anhydride. To a solution of the mixed anhydride in chloroform was added triethylamine and O-benzylhydroxylamine hydrochloride to obtain O-benzyl-4-pentenohydroxamic acid (1.2.6.5). The double bond was oxidized using osmium tetroxide/N-methylmorpholine oxide to give the diol (1.2.6.6). The terminal hydroxyl group was then protected with t-butyldimethylsilylchloride in the usual way to yield (1.2.6.7). The secondary hydroxyl group was tosylated using pyridine/p-toluenesulfonyl chloride. Cyclization of (1.2.6.8) to the corresponding pyrrolidone (1.2.6.9) was effected by using sodium carbonate in methanol. The protecting silyl group was removed by treatment with tetraethylammonium fluoride. The title compound (1.2.6.3) was prepared by reacting the latter compound (1.2.6.10) with pyridine/p-toluenesulfonyl chloride in the usual way.

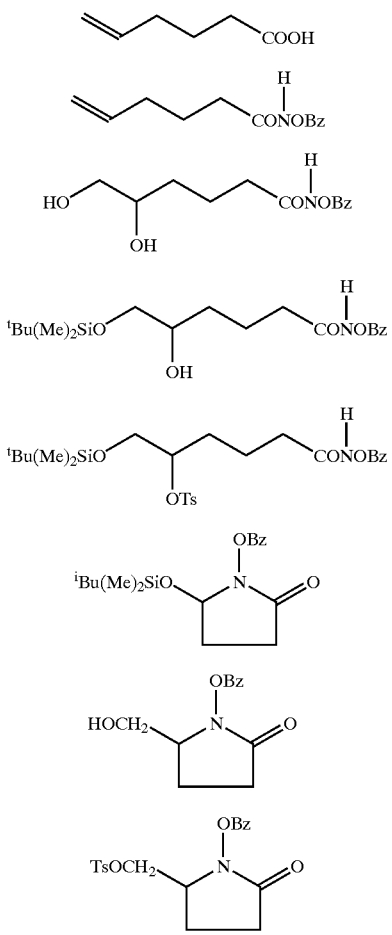

1.2.6.4

1.2.6.5

1.2.6.6

1.2.6.7

1.2.6.8

1.2.6.9

1.2.6.10

1.2.6.3

1.2.6.11 5-Bromo-1-benzyloxy-2-pyrrolidone

This compound was prepared in several steps. Butyrolactone was reacted with PBr3/Br2 to obtain the dibromobutyrylbromide (1.2.6.12). This compound with O-benzylhydroxylamine yielded the protected dibromohydroxamic acid (1.2.6.13). Cyclization was effected by base to give the cyclic protected hydroxamic acid (1.2.6.11).

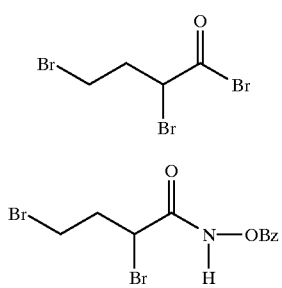

1.2.6.12

1.2.6.13

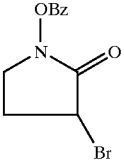

1.2.6.11

1.2.7 Preparation of N-Alkyl-O-Benzylchloroacetohydroxamic Acids

This class of compounds was prepared from chloroacetyl chloride and the suitable N-Alkylhydroxylamine followed by O-benzylation with benzyl bromide. In certain instances the O-benzyl alkylhydroxylamine was used as the starting material. O-Methyl chloroacetoxyhydroxamic acid was prepared employing O-methylhydroxylamine as starting material.

1.2.7.1 O-Benzyl-N-Methyl Chloroacetohydroxamic acid, ClCH$_2$CON(Me)(OBz).

1.2.7.2 O-Benzyl-N-isopropyl-Chloroacetohydroxamic acid, ClCH$_2$CON($^i$Pr)(OBz).

1.2.7.3 O-Benzyl-N-tert-butyl-Chloroacetohydroxamic acid, ClCH$_2$CON($^t$Bu)(OBz).

1.2.7.4 O-Benzyl Chloroacetohydroxamic acid, ClCH$_2$CONH(OBz)

1.2.7.5 O-Methyl chloroacetohydroxamic acid, ClCH$_2$CONH(OMe)

1.3 Synthesis of Chelators (Ligands)

1.3.1 Synthesis of Polyaza Ligands with Pendant Arms Containing β-Hydroxy Groups and Their Derivatives.

This family of compounds was prepared by reacting polyaza free bases with epoxides or halohydrines in water or alcohol solvents.

1.3.1.1 N,N',N''-Tris (2-hydroxy-3-isopropoxypropyl)-1,4,7-Triazacyclononane

From 1,4,7-triazacyclononane (1.1.3) and d,l-glycidyl isopropyl ether (1.2.1.2).

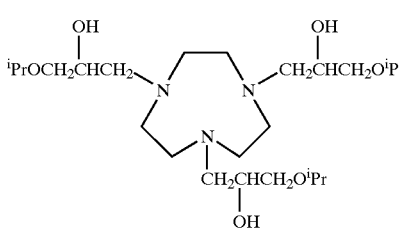

1.3.1.1

1.3.1.2 (R,R,R) N,N',N''-Tris(2-hydroxy-3-isopropoxypropyl)-1,4,7-triazacyclononane From 1,4,7-Triazacyclononane (1.1.3) and (2R) glycidyl isopropyl ether (1.2.1.3).

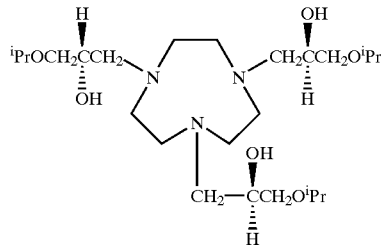

1.3.1.2

1.3.1.3 (S,S,S) N,N',N''-Tris(2-hydroxy-3-isopropoxypropyl)-1,4,7-triazacyclononane From 1,4,7-Triazacyclononane and (2S) glycidyl isopropyl ether (1.2.1.4).

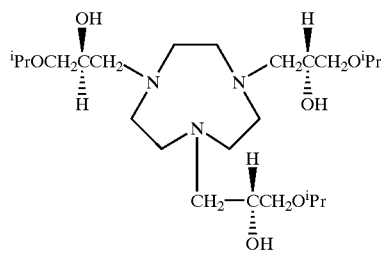

1.3.1.3

1.3.1.4 N,N',N''-Tris(2-hydroxy-3-t-butoxypropyl)-1,4,7-triazacyclononane

From 1,4,7-Triazacyclononane (1.13) and (d,l) glycidyl-t-Butyl ether (1.2.1.5).

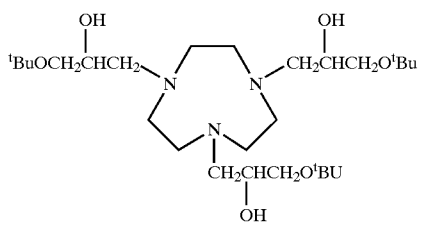

1.3.1.4

1.3.1.5 (R,R,R) N,N',N''-Tris(2-hydroxy-3-t-butoxypropyl)-1,4,7-triazacyclononane From 1,4,7-triazacyclononane (1.1.3) and (R) glycidyl t-Butyl ether (1.2.1.6).

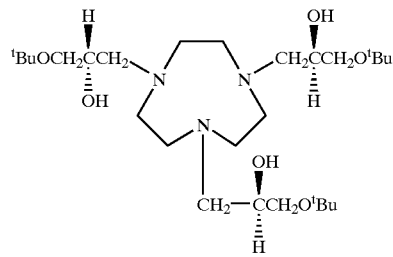

1.3.1.5

1.3.1.6 N,N',N''-Tris(2-hydroxy-3methoxypropyl)-1,4,7-triazacyclononane

From 1,4,7-Triazacyclononane (1.1.3) and (d,l) glycidyl methyl ether (Commercially Available).

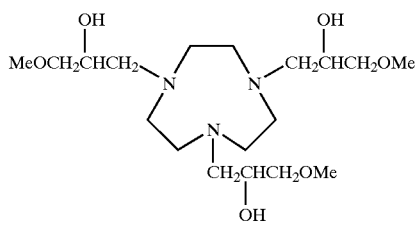

1.3.1.6

1.3.1.7 N,N',N''-Tris(2,3-dihydroxypropyl)-1,4,7-triazacyclononane

From 1,4,7-triazacyclononane (1.1.3) and 1-bromo-2,3-dihydroxypropane (Commercially Available) and excess of potassium carbonate or 1-chloro-2,3-dihydroxypropane (Commercially Available) and base.

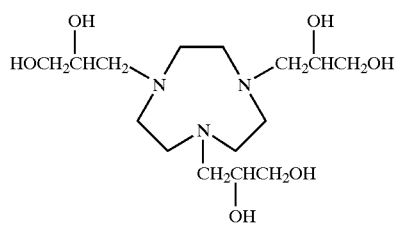

1.3.1.7

1.3.1.8 N,N',N''-Tris(1-methoxy-2-hydroxy-2-methylpropyl)-1,4,7-triazacyclononane From 1,4,7-Triazacyclononane (1.1.3) and (d,l) 3,3-Dimethyl-2-methoxy oxirane (1-methoxy-2-methylpropylene, commercially available).

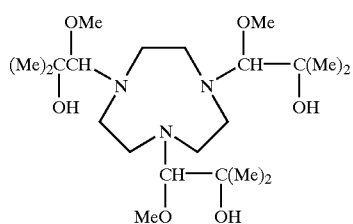
1.3.1.8

1.3.1.9 N,N',"-Tris(2-hydroxy-3-allyloxypropyl)-1,4,7-triazacyclononane

From 1,4,7-Triazacyclononane (1.1.3) and (d,l) glycidyl allyl ether (1.2.1.7).

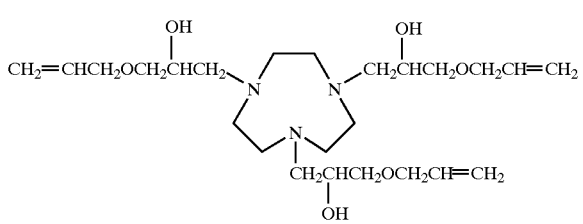
1.3.1.9

1.3.1.10 N,N',N"-Tris(2-hydroxy-3-phenoxypropyl)-1,4,7-triazacyclononane

From 1,4,7-Triazacyclononane (1.1.3) and (d,l) glycidyl phenyl ether (1.2.1.8).

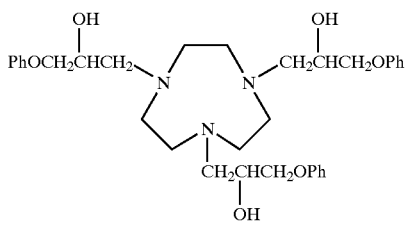
1.3.1.10

1.3.1.11 N,N',N"-Tris(2-hydroxy-2,2-diethoxymethylene)ethyl-1,4,7-triazacyclononane From 1,4,7-triazacyclononane (1.1.3) and 2,2-Bis-ethoxymethyl oxirane(1.2.2.1).

1.3.1.11

1.3.1.12 N,N',N"-Tris(2-hydroxy-2,2-dimethoxymethyl)ethyl-1,4,7-triazacyclononane From 1,4,7-triazacyclononane (1.1.3) and 2,2-Bis-methoxyoxymethyl oxirane (1.2.2.2).

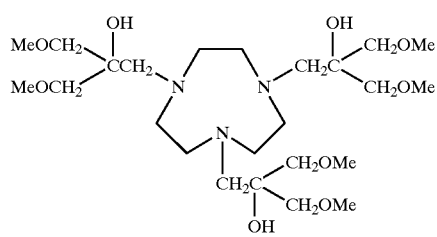
1.3.1.12

1.3.1.13 N,N',N"-Tri(2-hydroxy-(2,2-diisopropyloxymethyl)ethyl-1,4,7-triazacyclononane From 1,4,7-triazacyclononane (1.1.3) and 2,2-Bis-Isopropoxymethyl oxirane (1.2.2.3).

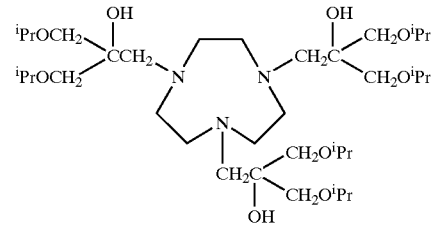
1.3.1.13

1.3.1.14 N,N',N"-Tris[2-hydroxy-bis(2-furfuryloxym)ethyl)ethyl]-1,4,7-triazacyclononane From 1,4,7-triazacyclononane (1.1.3) and 2,2-Bis(furfuryloxymethyl)oxirane (1.2.2.4).

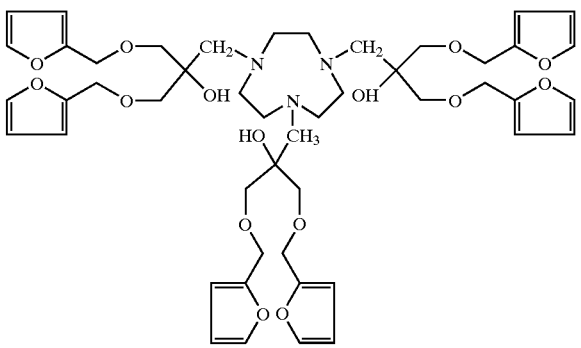
1.3.1.14

1.3.1.15 N,N',N"-Tris(3-hydroxy-1,5-dioxacycloheptyl-3-methyl)-1,4,7-triazacyclononane From 1,4,7-Triazacyclononane (1.1.3) and oxiranespiro-3-(1,5-dioxacycloheptane) (1.2.3.1).

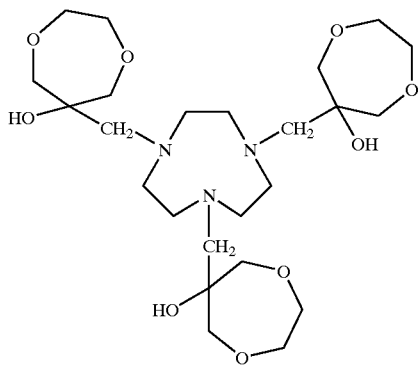

1.3.1.15

1.3.1.16 N,N',N''-Tris[(3-Hydroxy-7,7-dimethyl-1,5-dioxacyclooct-3-yl)-methyl]-1,4,7-triazacyclononane.

From 1,4,7-Triazacyclononane (1.1.3) and oxiranespiro-3-(1,5-dioxa-7,7-dimethylcycloociane) (1.2.3.2).

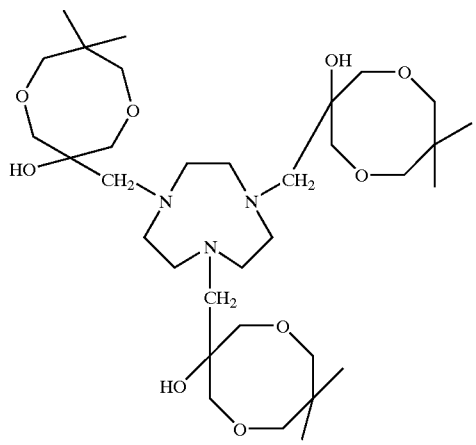

1.3.1.16

1.3.1.17 N,N',N''-Tris[(3-hydroxy-7-methyl-1,5-dioxacyclohept-3-yl)methyl]-1,4,7-triazacyclononane.

From 1,4,7-Triazacyclononane (1.1.3) and Oxiranespiro-3-(1,5-dioxa-6-methylcycloheptane (1.2.3.3).

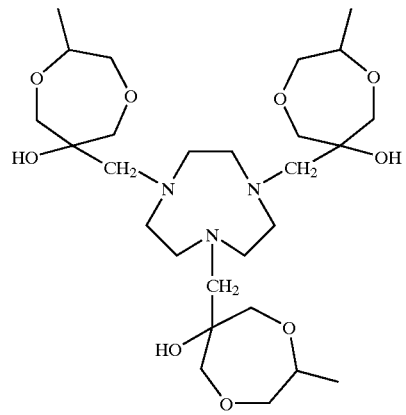

1.3.1.17

1.3.1.18 N,N',N''-Tris[(3-hydroxy-6,6,7,7-tetramethyl-1,5-dioxacyclohept-3-yl)methyl]-1,4,7-Triazacyclononane From 1,4,7-Triazacyclononane (1.1.3) and oxiranespiro-3-(1,5-dioxa-6,6,7,7-tetramethylcycloheptane) (1.2.3.4).

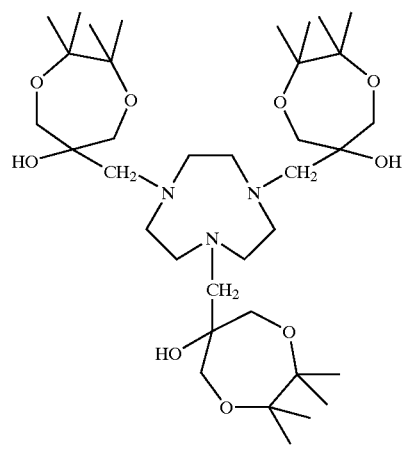

1.3.1.18

1.3.1.19 N,N',N''-Tris[(3-hydroxy-benzo[b]-1,5-dioxacycloheptyl)methyl]1,4,7-triazacyclononane
From 1,4,7-triazacyclononane (1.1.3) and oxiranespiro-3-(benzo[b]-1,5-dioxacycloheptane) (1.2.3.5).

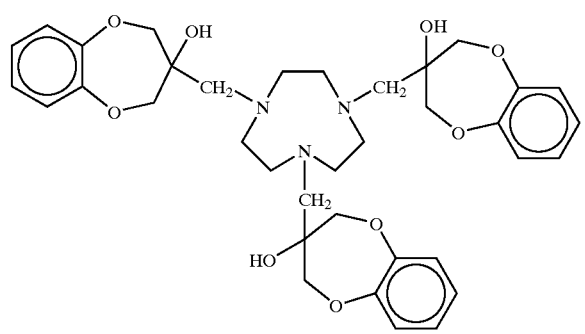

1.3.1.19

1.3.1.20 N,N',N''-Tris[(3-hydroxy-1,5-dioxacyclooctane-3-yl)methyl]-1,4,7-triazacyclononane From 1,4,7-triazacyclononane (1.1.3) and oxiranespiro-3-(1,5-dioxacyclooctane) (1.2.3.6).

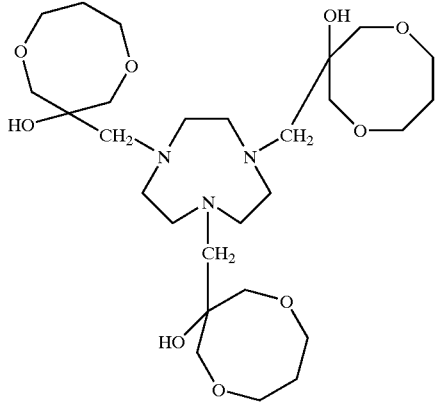

1.3.1.20

1.3.1.21 N,N',N''-Tris(2-hydroxy-2-methylpropyl)-1,4,7-Triazacyclononane

From 1,4,7-Triazacyclononane (1.1.3) and 2,2-Dimethyl oxirane (1.2.4.1)

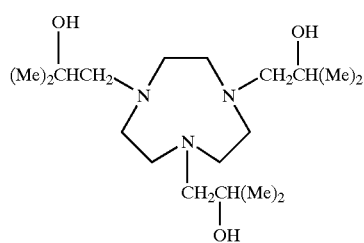

1.3.1.21

1.3.1.22 N,N',N''-Tris[(4-fluoro-2-hydroxy-3-i-propyl-4-methyl)pentyl]-1,4,7-triazacyclononane From 1,4,7-triazacyclononane (1.1.3) and 2-isopropyl-2-(1-fluoro-1-methylethyl)oxirane (1.2.4.2).

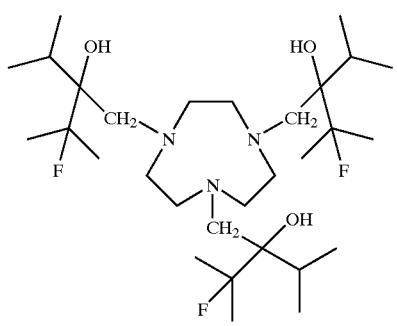

1.3.1.22

1.3.1.23 N,N',N''-Tris-[12-hydroxy-3-(1-fluoroethyl)-4-hydroxypentyl]-1,4,7-triazacyclononane From 1,4,7-triazacyclononane (1.1.3) and 2-(1-trimethylsilyloxyethyl)-2-(1-fluoroethyl)oxirane (1.2.4.8).

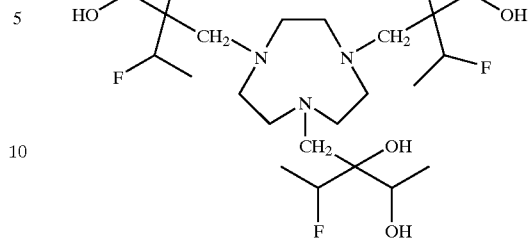

1.3.1.23

1.3.1.24 N,N',N''-Tris[2-hydroxy-2-(1-fluoroethyl)-2-(1-methoxyethyl)ethyl]-1,4,7-triazacyclononane From 1,4,7-triazacyclononane (1.1.3) and 2-(1-Fluoroethyl)-2-(1-methoxyethyl)oxirane (1.2.4.19).

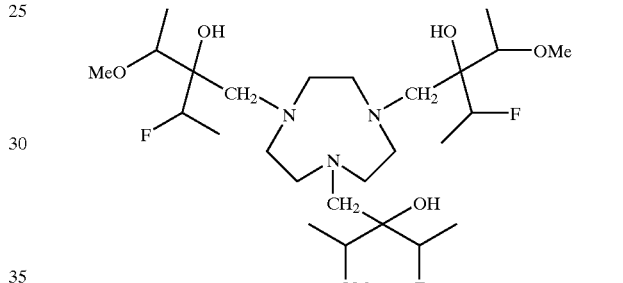

1.3.1.24

1.3.1.25 N,N',N''-Tris(2-hydroxy-2-ethyl-3-methoxy butyl)-1,4,7-triazacyclononane From 1,4,7-triazacyclononane (1.1.3) and 2-ethyl-2-(1-methoxyethyl)oxirane (1.2.4.24).

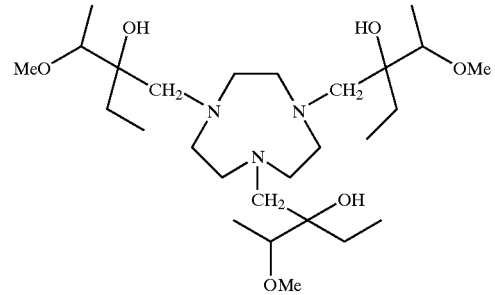

1.3.1.25

1.3.1.26 N,N',N''-Tris(2,3-dihydroxy-2-ethyl)butyl]-1,4,7-Triazacyclononane

From 1,4,7-triazacyclononane (1.1.3) and 2-ethyl-2-(1-trimethylsilyloxyethyl)oxirane (1.2.4.28).

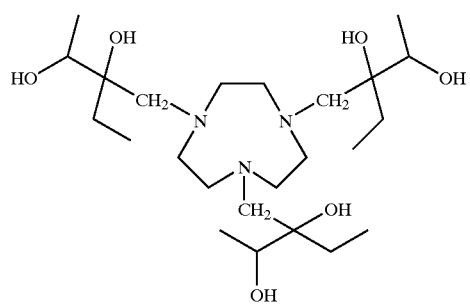

1.3.1.26

1.3.1.27 N,N',N"-Tris[2-hydroxy-2,2-bis(1-fluoro ethyl)ethyl]-1,4,7-triazacyclononane From 1,4,7-triazacylononane (1.1.3) and 2,2-bis(1-fluoroethyl) oxirane (1.2.4.33).

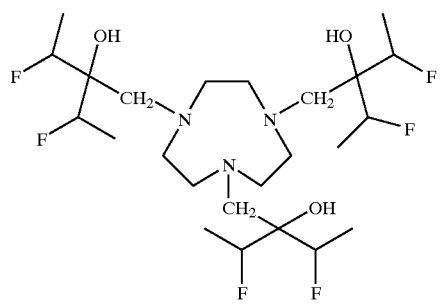

1.3.1.27

1.3.1.28 N,N',N"-Tris[2-hydroxy-2,2-bis(1-methoxyethyl)ethyl]-1,4,7-triazacyclononane From 1,4,7-Triazacyclononane (1.1.3) and 2,2-(1-methoxyethyl) oxirane (1.2.4.37).

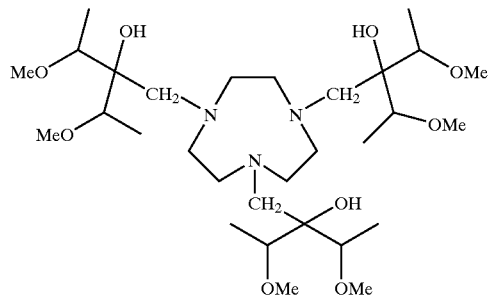

1.3.1.28

1.3.1.29 N,N',N"-Tris[(3,3-dimethyl-2-hydroxy)butyl]-1,4,7-triazacyclononane From 1,4,7-Triazacyclononane (1.1.3), 1-Bromo-2-hydroxy-3,3- dimethylbutane (1.2.6.1) and sodium carbonate.

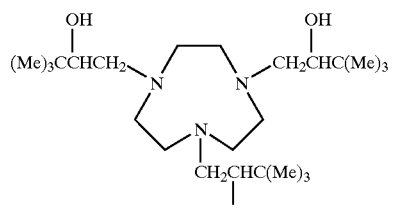

1.3.1.29

1.3.1.30 N,N',N"-Tris(2-hydroxypropyl)-1,4,7-triazacyclononane

From 1,4,7-triazacyclononane (1.1.3) and propylene oxide.

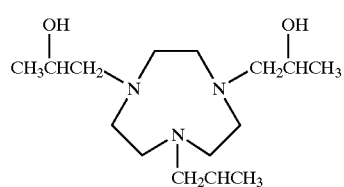

1.3.1.30

1.3.1.31 N, N',N"-Tris(2,2-dimethoxyethanyl)-1,4,7-triazacyclononane

From 1,4,7-triazacyclononane (1.1.3), 1-chloro-2,2-dimethoxyethane (Commercially Available) and sodium carbonate.

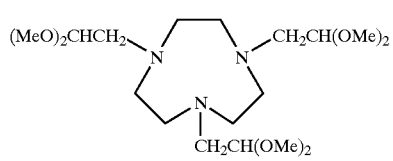

1.3.1.31

1.3.1.32 N,N',N"-Tris(2-hydroxycyclopentan-1-yl)-1,4,7-triazacyclononane

From 1,4,7-triazcyclononane (1.1.3), 1,2-epoxycyclopentane (Commercially Available) and sodium carbonate.

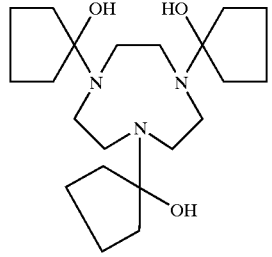

1.3.1.32

1.3.1.33 N,N',N"-Tris(2-hydroxycyclohexane-1-yl)-1,4,7-triazacyclononane

From 1,4,7-triazacyclononane (1.1.3), 1,2-epoxycyclohexane (Commercially Available) and sodium carbonate.

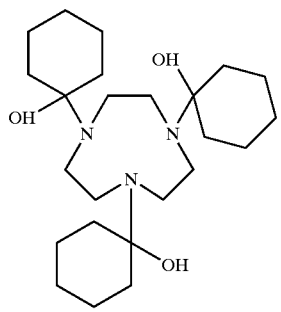

1.3.1.34 N,N',N''-Triallyl-1,4,7-Triazacyclononane

From 1,4,7-triazacyclononane (1.1.3), sodium hydride and allyl bromide.

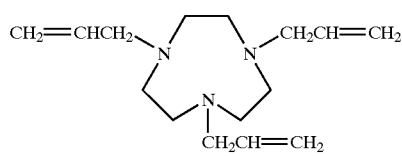

1.3.1.35 N,N',N''-Tris[(3-chloro-2-hydroxy)propyl)]-1,4,7-Triazacyclononane

From N,N',N''-triallyl-1,4,7-triazacyclononane(1.3.1.34) and aqueous chlorine.

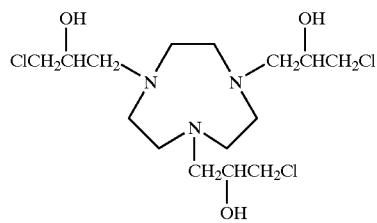

1.3.1.36 1,2-Bis-(N,N'-di-2-hydroxyethyl-1,4,7-triazacyclononane-1-yl)ethane

From 1,2-bis-(1,4,7-triazacyclononane-1-yl)ethane polyhydrobromide and ethylene oxide.

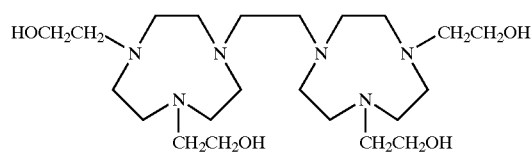

1.3.1.37 N,N',N'',N'''-Tetrakis-(2-hydroxyethyl)-1,4,7,10-tetraazacyclododecane

From 1,4,7,10-Tetraazacyclododecane (1.1.4) and bromoethanol.

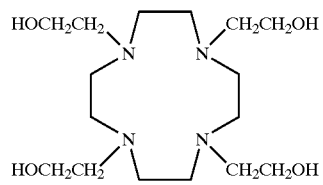

1.3.1.38 N,N',N'',N'''-Tetrakis(2,3-dihydroxypropyl)-1,4,7,10-tetraazacyclotetradecane From 1,4,7,10-tetraazacyclotetradecane (1.1.4), 1-chloro-2,3-propanediol (Commercially Available) and base.

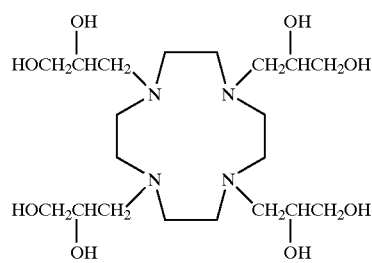

1.3.1.39 4,10-Bis(2-Hydroxypropyl)-1,4,7,10-tetraazabicyclo[5.5.2]tetradecane

From 1,4,7,10-tetraazabicyclo[5.5.2]tetradecane (1.1.4) and propylene oxide.

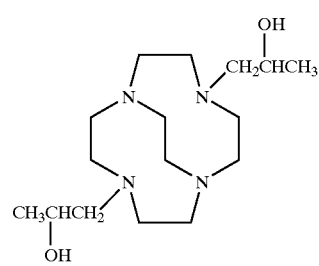

1.3.1.40 4,10-Bis-(2-hydroxyethyl)-1,4,7,10-tetraazabicyclo[5.5.2]tetradecane

From 4,10-Bis(dimethoxycarbonylmethyl)-1,4,7,10-tetraazabicyclo[5.5.2]tetradecane (1.3.6.8) and lithium aluminum hydride.

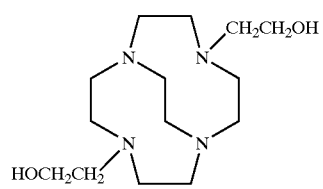

1.3.1.41 4,10-Bis[(2-Hydroxy-2-phenyl)ethyl]-1,4,7,10-tetraazabicyclo[5.5.2]tetradecane From 1,4,7,10-Tetraazabicyclo[5.5.2]tetradecane (1.1.4) and styrene oxide.

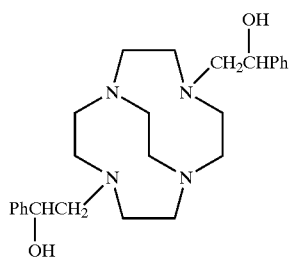

1.3.1.42 4,10-Bis-(2,3-dihydroxypropyl)-14,7,10-tetraazabicyclo[5.5.2]tetradecane From 1,4,7,10-tetraazabicyclo[5.5.2]tetradecane (1.1.4) and glycidol.

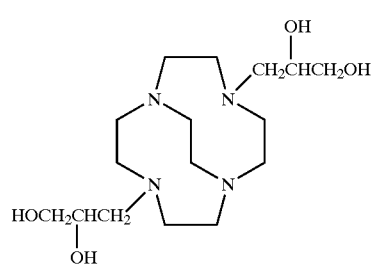

1.3.1.43 N,N'N'',N'''-Tetrakis-(2,3-dihydroxypropyl)-1,4,8,11-tetraazacyclohexadecane From cyclam (1.1.5) and glycidol.

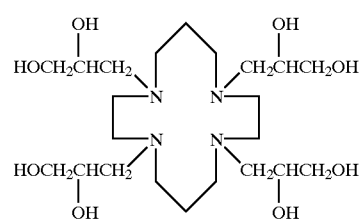

1.3.1.44 cis, trans N,N,N',N'-Tetrakis(2,3-dihydroxypropyl)-1,2-diaminocyclohexane From cis,trans 1,2-diaminocyclohexane (Commercially Available) and glycidol.

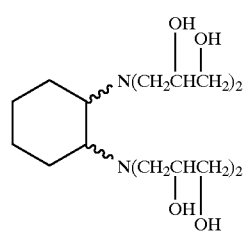

1.3.1.45 trans N,N,N',N'-Tetrakis(2,3-dihydroxypropyl)-1,2-diaminocyclohexane

From trans-1,2-diaminocyclohexane (Commercially Available) and glycidol.

1.3.1.46 N, N, N',N'-Tetrakis(2,3-dihydroxypropyl)-ethylenediamine

From ethylenediamine (1.1.0) and glycidol.

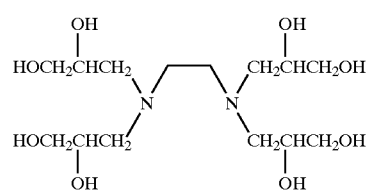

1.3.1.47 N,N,N',N'',N'''-Pentakis(2,3-dihydroxypropyl)-diethylenetriamine

From diethylenetriamine (1.1.1), 1-chloro-2,3-propanediol and base.

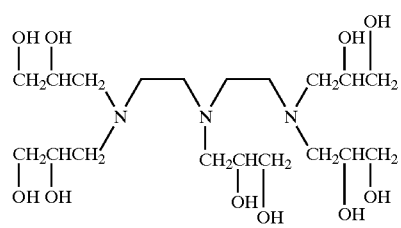

1.3.1.48 N,N,N',N'',N''',N'''-Hexaakis(2,3-dihydroxypropyl)triethylenetetramine

From triethylenetetramine (1.1.2) and glycidol.

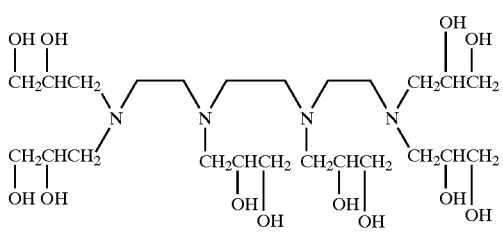

1.3.1.49 N,N,N',N'-Tetrakis(2,3-dihydroxypropyl)-1,2-diamino-2-methylpropane From 1,2-diaminomethylpropane and glycidol.

1.3.1.49

1.3.1.50 N,N,N',N'-Tetrakis(2,3-dihydroxypropyl)-1,2-diaminopropane

From 1,2-diaminopropane and glycidol.

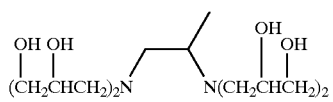
1.3.1.50

1.3.1.51 N,N',N''-Tris(2,3-diacetoxypropyl)-1,4,7-triazacyclononane

From 1.3.1.7 and Py/Ac$_2$O.

1.3.1.51

1.3.1.52 N,N',N''-tris(Dimethyl-2,3-isopropylidene propyl)-1,4,7-triazacyclononane From 1.3.1.7 and 2,2-dimethoxypropane/p-toluenesulfonic acid.

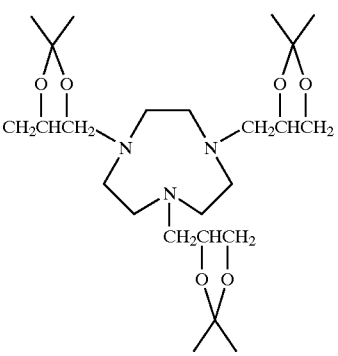
1.3.1.52

1.3.1.53 4,10-(2-Diacetoxyoxypropyl)-1,4,7,10-tetraazabicyclo[5.5.2]tetradecane From 1.3.1.39 and Py/Ac$_2$O.

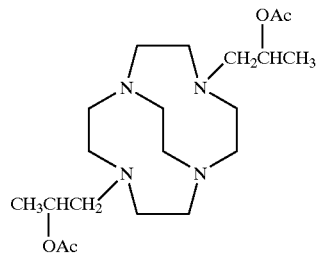
1.3.1.53

1.3.1.54 N,N',N''-Tris[(2,4-dihydroxy-3-isopropyl-4-methyl)pentyl]-1,4,7-triazacyclononane From 1,4,7-triazacyclononane (1.1.3) and 2,2-bis(hydroxymethyl) oxirane.

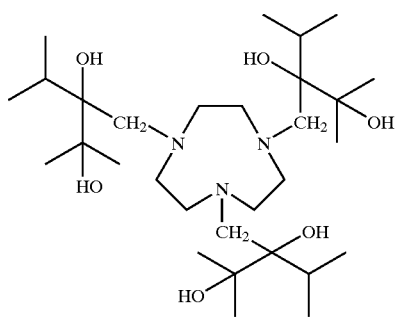
1.3.1.54

1.3.1.55 N,N',N''-Tris-[2-hydroxy-(2,2-dihydroxymethyl)ethyl]-1,4,7-triazacyclononane From 1,4,7-triazacyclononane (1.1.3) and 2,2-bis(hydroxymethyl) oxirane (1.2.2.5).

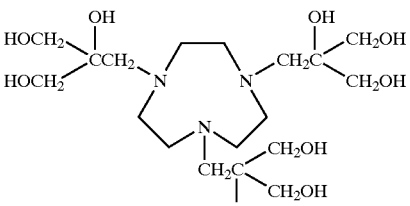
1.3.1.55

1.3.2 Synthesis of Polyaza Ligands with Alkylphosphonate Mono- and Di-Esters Pendant Arms.

1.3.2.1 Preparation

Chelators which have three identical methylene phosphonate diester arms were prepared by reacting the trihydrobromide polyaza bases with formaldehyde and dialkylphosphite. The hexa-ester was hydrolized to the tri-ester by heating with NaOH dissolved in the appropriate alcohol (the same R group as in the dialkylphosphite). In some cases products were obtained by reacting the amine base with haloalkylphosphonates or epoxyphosphonates.

1.3.2.1 N,N',N'-Tris(dibutylphosphorylmethyl)-1,4,7-triazacyclononane

From 1,4,7-triazacyclononane (1.1.3) trihydrobromide, formaldehyde solution and di-n-butyl phosphite (1.2.5.1).

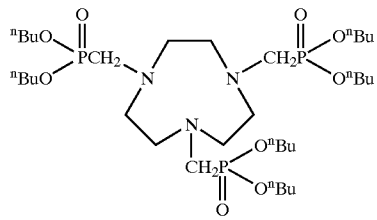

1.3.2.1

1.3.2.2 N,N',N''-Tris(dihydroxyphosphorylmethyl mono butyl ester)-1,4,7-triazacyclononane From N,N',N''-tris(dibutylphosphorylmethyl)-1,4,7-triazacyclononane (1.3.2.1) and KOH/butanol.

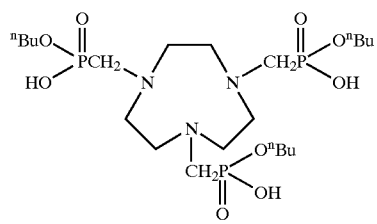

1.3.2.2

1.3.2.3 N,N',N''-Tris(diethylphosphorylmethyl)-1,4,7-triazacyclononane

From 1,4,7-triazacyclononane (1.1.3) trihydrobromide, formaldehyde solution and diethyl phosphite (Commercially Available).

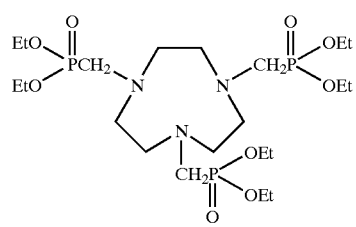

1.3.2.3

1.3.2.4 N,N',N''-Tris(dihydroxyphosphorylmethyl monoethyl ester)-1,4,7-triazacyclononane From N, N', N''-tris(diethylphosphorylmethyl)-1,4,7-triazacyclononane (1.3.2.3) and NaOH/EtOH.

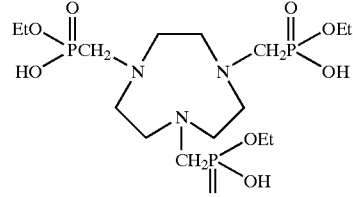

1.3.2.4

1.3.2.5 N,N',N''-Tris(dioctylphosphorylmethyl)-1,4,7-triazacyclononane

From 1,4,7-triazacyclononane (1.1.3), formaldehyde and dioctylphosphite (1.2.5.2).

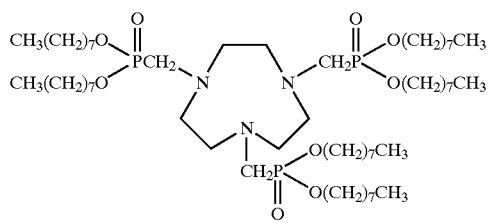

1.3.2.5

1.3.2.6 N,N',N''-Tris(dihydroxyphosphorylmethyl monooctyl ester)-1,4,7-triazacyclononane From 1.3.2.5 and NaOH in octyl alcohol.

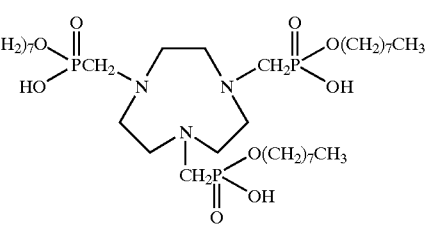

1.3.2.6

1.3.2.7 N,N',N''-Tris(diisobutylphosphorylmethyl)-1,4,7-triazacyclononane

From 1,4,7-Triazacyclononane (1.1.3), formaldehyde and diisobutylphosphite (1.2.5.3).

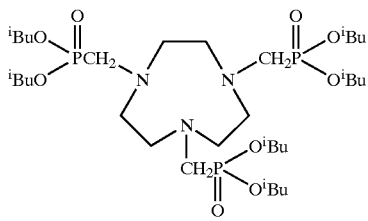

1.3.2.7

1.3.2.8 N,N',N''-Tris(dihydroxyphosphorylmethyl monoisobutyl ester)-1,4,7-triazacyclononane From 1.3.2.7 and NaOH in isobutyl alcohol.

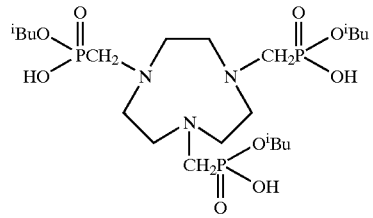

1.3.2.8

1.3.2.9 N,N',N''-Tris(dibenzylphosphorylmethyl)-1,4,7-triazacyclononane

From 1,4,7-Triazacyclononane (1.1.3), formaldehyde and dibenzylphosphite (1.2.5.4).

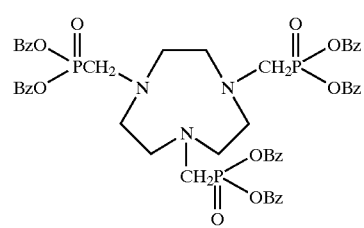

1.3.2.9

1.3.2.10 N,N',N''-Tris(diethylphosphorylethyl)-1,4,7-triazacyclononane

From 1,4,7-triazacyclononane (1.1.3) trihydrobromide, potassium carbonate and diethyl(2-bromoethyl)phosphonate (1.2.5.5).

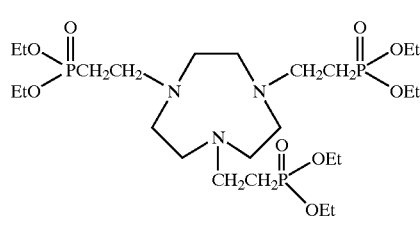

1.3.2.10

1.3.2.11 N,N',N'',N'''-Tetrakis(diethylphosphorylmethyl)-1,4,7,10-Tetraazacyclodecane From 1,4,7,10-Tetraazacyclododecane (1.1.4) trihydrobromide, formaldehyde and diethylphosphite (commercially available).

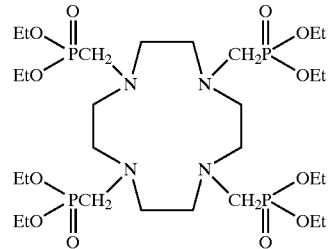

1.3.2.11

1.3.2.12 N,N',N'',N'''-Tetrakis(diethylphosphorylethyl)-1,4,7,10-tetraazacyclododecane From 1,4,7,10-tetraazacyclododecane (1.1.4) trihydrobromide, potassium carbonate and diethyl(2-bromoethyl)phosphonate (1.2.5.5).

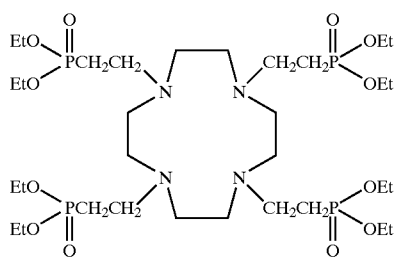

1.3.2.12

1.3.2.13 4,10-Bis(diethylyphosphorylethyl)-1,4,7,10-tetraazabicyclo[5.5.2]tetradecane From 1,4,7,10-tetraazabicyclo[5.5.2]tetradecane (1.1.20) dihydrobromide, potassium carbonate and diethyl(2-bromoethyl)phosphonate (1.2.5.5).

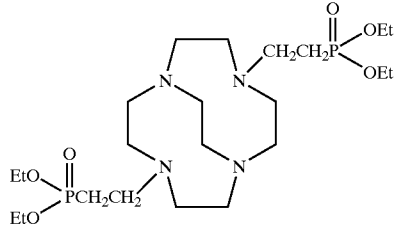

1.3.2.13

1.3.2.14 4,10-Bis(diethylphosphoryl methyl)-1,4,7,10-tetraazabicyclo[5.5.2]tetradecane From 1,4,7,10-tetraazabicyclol[5.5.2]tetradecane (1.1.20) trihydrobromide, formaldehyde and diethylphosphite (commercially available).

1.3.2.14
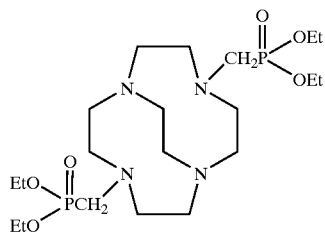

1.3.2.15 N,N',N''-Tris(diethylphosphorylmethyl)-1,4,7,10,13-pentaazabicyclo[8.5.2]heptadecane From 1,4,7,10,13-pentaazabicyclo[8.5.2]heptadecane (1.1.25), formaldehyde and diethylphosphite (commercially available).

1.3.2.15
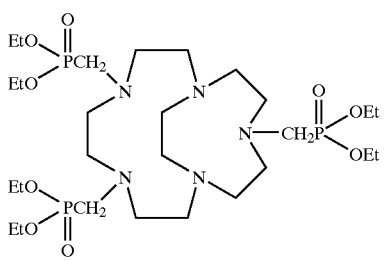

1.3.3 Synthesis of Polyaza Ligands with Identical Alkylphosphonic Acid Pendant Arms These compounds were prepared by either hydrotizing the ester groups of the compounds described under 1.3.2, or from the polyaza base, formaldehyde and phosphorous acid.

1.3.3.1 1,2-Bis(N,N'-bis(dihydroxyphosphrylmethyl)-1,4,7-triazacyclononan-1-yl)ethane From 1,2-bis-(1,4,7-triazacyclononan-1-yl)ethane (1.1.28), formaldehyde and phosphorous acid.

1.3.3.1
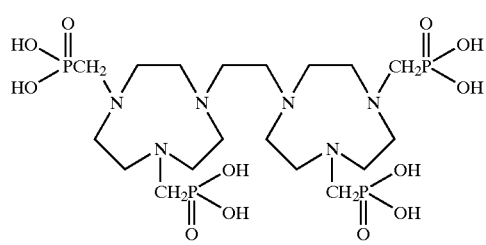

1.3.3.2 1,2-Bis(N,N'-bis(dihydroxyphosphorylmethyl)-1,4,7-triazacyclononan-1-yl)propane From 1,2-Bis-(1,4,7-triazacyclononan-1-yl)propane (1.1.19), formaldehyde and phosphorous acid.

1.3.3.2
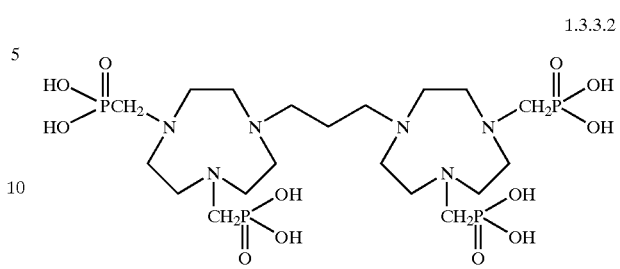

1.3.3.3 4,10-Bis(dihydroxyphosphorylmethyl)-1,4,7,10-tetraazabicyclo[5.5.2]tetradecane From 1,4,7,10-Tetraazabicyclo[5.5.2]tetradecane (1.1.20) trihydrobromide, formaldehyde and phosphorous acid.

1.3.3.3
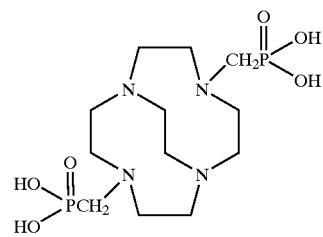

1.3.3.4 4,7,13-Tris(dihydroxyphosphorylmethyl)-1,4,7,10,13-pentaazabicyclo[8.5.2]heptadecane From hydrolysis of 1,4,7,13-tris(diethylphosphorylmethyl)-1,4,7,10,13-pentaazabicyclo[8.5.2]heptadecane (1.3.2.15) by HCl.

1.3.3.4
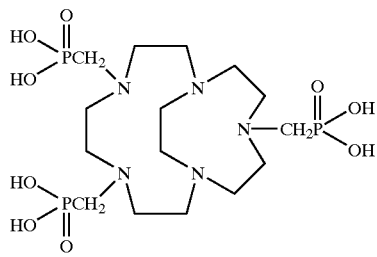

The following compounds were prepared from the corresponding diesters by hydrolysis with HCl:

1.3.3.5 N,N',N''-Tris(dihydroxyphosphorylethyl)-1,4,7-triazacyclononane 1.3.3.5
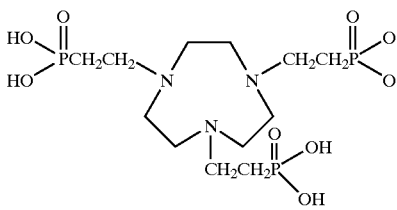

1.3.3.6 N,N',N'',N'''-Tetrakis(dihydroxyphosphorylethyl)-1,4,7,10-tetraazacyclododecane

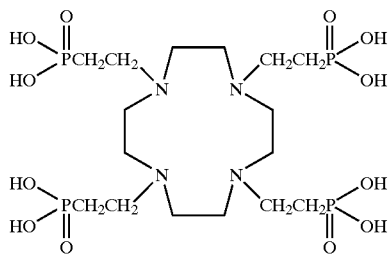

1.3.3.6

1.3.3.7 4,10-Bis(dihydroxyphosphorylethyl)-1,4,7,10-tetraazabicyclo[5.5.2]tetradecane

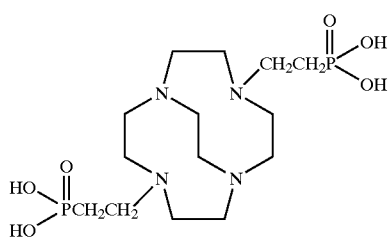

1.3.3.7

1.3.4 Synthesis of Polyaza Ligands with Pendant Arms Containing Phosphonate Esters and Acids with Alpha Substituent Groups Alkyl or aryl groups α to the phosphonate moiety were prepared by alkylation of the corresponding ligand in the form of its dialkylphosphonate.

1.3.4.1 N,N',N''-Tris[α-dihydroxyphosporyl-α-benzyl)methyl]-1,4,7-Triazacyclononane From N,N',N''-Tris[(α-diethylphosporyl-α-benzyl)methyl]-1,4,7-triazacyclononane (U.S. Pat. No. 5,380,515) and trimethylsilyl iodide.

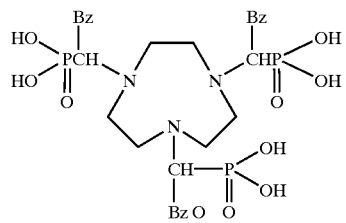

1.3.4.1

1.3.4.2 N,N',N''-Tris{[(diethylphosphoryl)-α-hydroxy]ethyl}-1,4,7-triazacyclononane From 1,4,7-triazacyclononane (1.1.3) and 2-diethylphosphoryl oxirane (1.2.5.7).

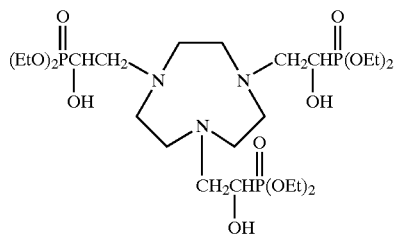

1.3.4.2

1.3.4.3 N,N',N''-Tris[dihydroxyphosphoryl-α-hydroxy)ethyl]-1,4,7-triazacyclononane From 1.3.4.2 and HCl.

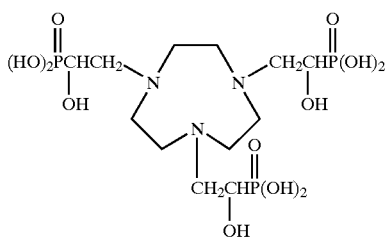

1.3.4.3

1.3.5 Synthesis of Polyaza Ligands with Pendant Arms Containing Hydroxamate Groups These compounds were prepared by reacting 1,4,7-tetraazacyclononane (1.1.3) trihydrobromide with a N-alkyl-O-benzyl chloroacetohydroxamic acid in the presence of a base. The free hydroxamic acid was obtained by removing the benzyl protecting group by hydrogenolysis.

1.3.5.1 N,N',N''-Tris[(N-methyl-N-benzyloxycarbamoyl)methyl]1,4,7-triazacyclononane From 1,4,7-triazacyclononane, sodium carbonate and O-benzyl-N-methyl chloroacetohydroxamate (1.2.7.1).

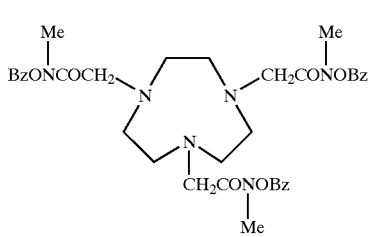

1.3.5.1

1.3.5.2 N,N',N''-Tris[(N-methyl-N-hydroxycarbamoyl)methyl]-1,4,7-triazacyclononane From N,N',N''-Tris[(N-methyl-N-benzyloxycarbamoyl)methyl]-1,4,7-triazacyclononane (1.3.5.1) and H₂ and Pd/C.

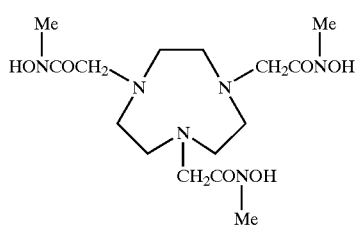

1.3.5.2

1.3.5.3 N,N',N''-Tris[(N-isopropyl-N-benzyloxycarbamoyl)methyl]-1,4,7-triazacyclononane From 1,4,7-Triazacyclononane trihydrobromide and chloroaceto-N-isopropyl-O-benzyl hydroxamate (1.2.7.2).

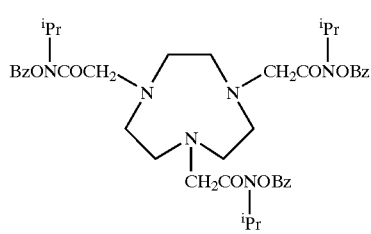

1.3.5.3

1.3.5.4 N,N',N''-Tris[(N-isopropyl-N-hydroxycarbamoyl)methyl]-1,4,7-triazacyclononane From 1.3.5.3 and $H_2$ and Pd/C.

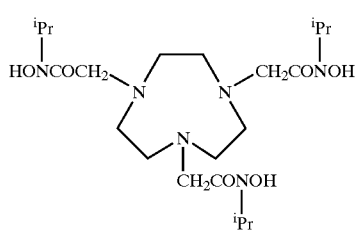

1.3.5.4

1.3.5.5 N,N',N''-Tris[(N-t-butyl-N-benzyloxycarbamoyl)methyl]-1,4,7-triazacyclononane From 1,4,7-triazacyclononane trihydrobromide and chloroaceto-N-t-butyl-O-benzyl hydroxamate (1.2.7.3).

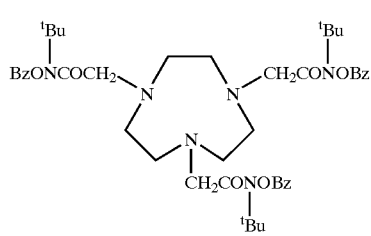

1.3.5.5

1.3.5.6 N,N',N''-Tris[(N-t-butyl-N-hydroxycarbamoyl)methyl]-1,4,7-triazacyclononane From 1.3.5.5, $H_2$ and Pd/C.

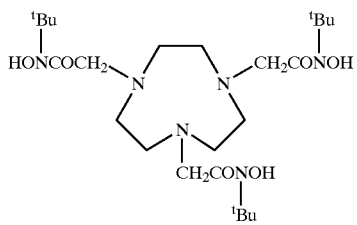

1.3.5.6

1.3.5.7 N,N',N''-Tris[(N-benzyloxycarbamoyl)methyl]-1,4,7-triazacyclononane

From 1,4,7-triazacyclononane (1.1.3) trihydrobromide and chloroaceto-O-benzyl hydroxamate (1.2.7.4).

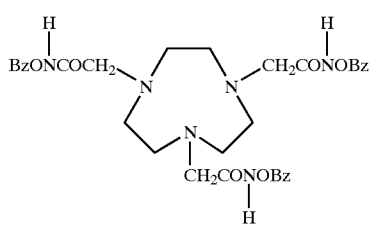

1.3.5.7

1.3.5.8 N,N',N''-Tris[(N-hydroxycarbamoyl)methyl]-1,4,7-triazacyclononane

From 1.3.5.7 and $H_2$ and Pd/C.

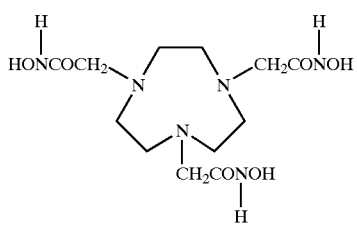

1.3.5.8

1.3.5.9 N,N',N''-Tris[(N-methoxycarbamoyl)methyl]-1,4,7-triazacyclononane

From 1,4,7-triazacyclononane (1.1.3) trihydrobromide and chloroaceto-O-methyl hydroxamate (1.2.7.5).

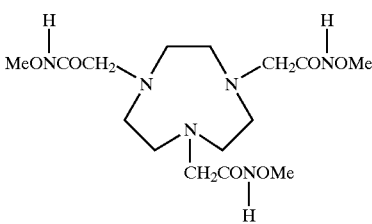

1.3.5.9

1.3.5.10 4,10-Bis[(N-benzyloxycarbamoyl-N-methyl)methyl]-1,4,7,10-tetraazabicyclo [5.5.2] tetradecane From 1,4,7,10-tetraazabicyclo[5.5.2]tetradecane (1.1.20) dihydrobromic acid, sodium carbonate and chloroaceto-O-benzyl hydroxamate (1.2.7.4).

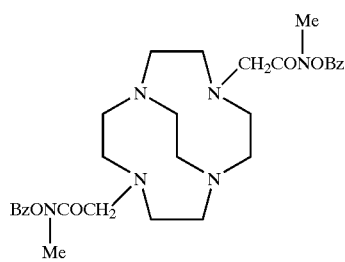
1.3.5.10

1.3.5.11 4,10-Bis[(N-hydroxycarbamoyl-N-methyl)methyl]-1,4,7,10-Tetraazabicyclo [5.5.2]tetradecane From 1.3.5.10 and $H_2$ and Pd/C.

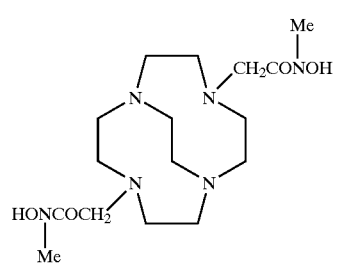
1.3.5.11

1.3.5.12 N,N',N''-Tris[(1-benzyloxy-2-pyrrolidone-5-yl)methyl]-1,4,7-triazacyclononane From 1,4,7-triazacyclononane (1.1.3), 5-(p-toluenesulfonyloxymethyl)-1-benzyloxy-2-pyrrolidone (1.2.6.3) and base.

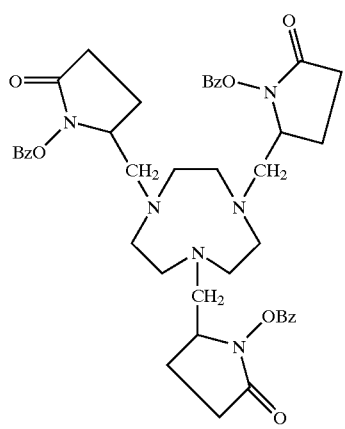
1.3.5.12

1.3.5.13 N,N',N''-Tris[(1-oxy-2-pyrrolidone-5-yl)methyl]-1,4,7-triazacyclononane From 1.3.5.12 and Pd/C (5%) and $H_2$.

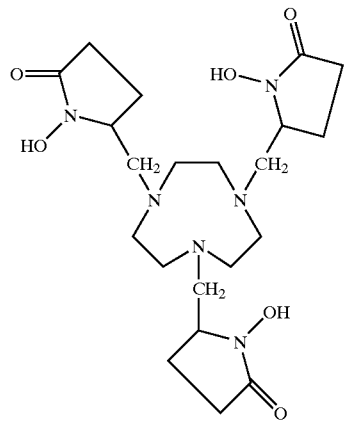
1.3.5.13

1.3.5.14 N,N',N''-Tris(1-benzyloxy-2-pyrrolidone-5-yl)-1,4,7-triazacyclononane From 1,4,7-triazacyclononane (1.1.3), 5-bromo-1-benzyloxy-2-pyrrolidone (1.2.6.11) and base.

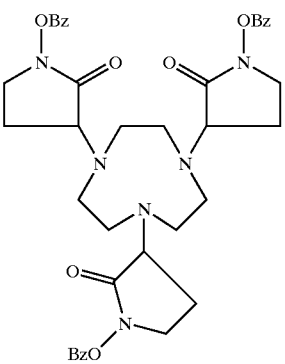
1.3.5.14

1.3.5.15 N,N',N''-Tris(1-oxy-2-pyrrolidone-5-yl)-1,4,7-triazacyclononane

From 1.3.5.14 and Pd/C (5%) and $H_2$.

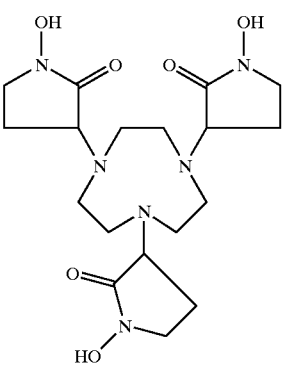
1.3.5.15

1.3.6 Synthesis of Polyaza Ligands with Pendant Arms Containing Carboxyl Groups And The Corresponding Esters Compounds were prepared by reacting polyaza bases with either halo carboxylic acids or by reductive alkylation with aldo or keto acids. The esters were prepared either by reacting directly with halo carboxylic acid esters or by reaction of the free acid with $SOCl_2$/alcohol.

1.3.6.1 N,N',N"-Tris(carboxymethyl)-1,4,7-triazacyclononane

From 1,4,7-triazacyclononane (1.1.3), glyoxylic acid and $H_2$/Pt.

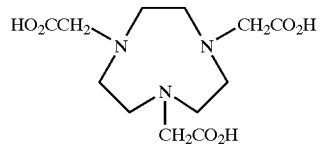

1.3.6.1

1.3.6.2 N,N',N"-Tris(methoxycarbonylmethyl-1,4,7-triazacyclononane

From N,N',N"-tris(carboxymethyl)-1,4,7-triazacyclononane in methanol and $SOCl_2$.

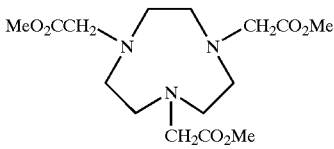

1.3.6.2

1.3.6.3 N,N',N"-Tris(α-methylcarboxymethyl)-1,4,7-Triazacyclononane

From 1,4,7-triazacyclononane (1.1.3), pyruvic acid and $H_2$/Pt.

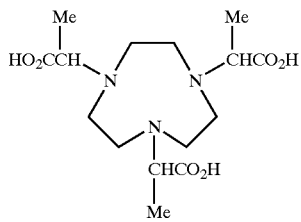

1.3.6.3

1.3.6.4 N,N',N"-Tris(methoxycarbonylmethyl-1,4,7-triazabicyclo-[7.4.0$^{8,13}$]tridecane From 1,4,7-Triazabicyclo[7.4.0$^{8,13}$]tridecane hydrobromide (1.1.14), glyoxylic acid and $H_2$/$PtO_2$ in methanol.

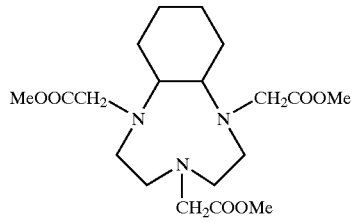

1.3.6.4

1.3.6.5 N-(α-methylcarboxymethyl)-1,4,7-triazabicyclo[7.4.0]tridecane

From 1,4,7-triazabicyclo[7.4.0$^{8, 13}$]tridecane (1.1.14), pyruvic acid and $H_2$/$PtO_2$.

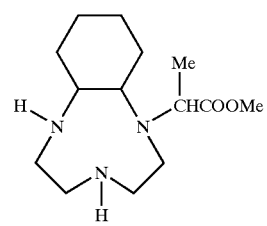

1.3.6.5

1.3.6.6 N,N',N"-Tris(ethoxycarbonylmethyl)-1,4,7-triazacyclo[7.4.0]tridecane From 1,4,7-triazabicyclo[7.4.0$^{8,13}$]tridecane (1.1.14), sodium methoxide and ethyl bromoacetate.

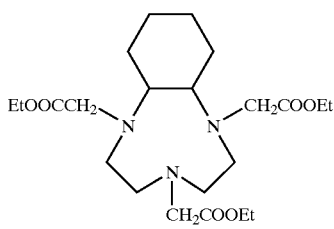

1.3.6.6

1.3.6.7 1,2-Bis-(4,7-carboxymethyl-1,4,7-triazacyclononan-1-yl)ethane

From 1,2-Bis(1,4,7-triazacyclononan-1-yl)ethane (1.1.28), chloroacetic acid and NaOH.

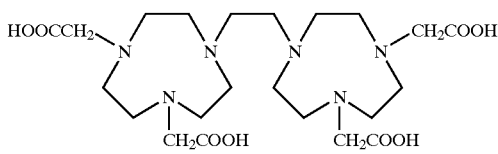

1.3.6.7

1.3.6.8 4,7-Bis(carboxymethyl)-1,4,7,10-tetraazabicyclo[5.5.2]tetradecane

From 1,4,7,10-tetraazabicyclo[5.5.2]tetradecane (1.1.22), chloroacetic acid and NaOH.

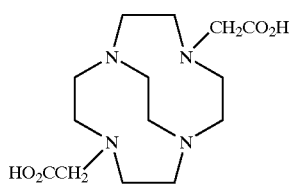

1.3.6.8

1.3.6.9 4,7-Bis(methoxycarboxymethyl)-1,4,7,10-tetraazabicyclo[5.5.2]tetradecane From 4,7-bis(carboxymethyl)-1,4,7,10-tetraazabicyclo[5.5.2]tetradecane (1.1.20) in MeOH/$H_2SO_4$.

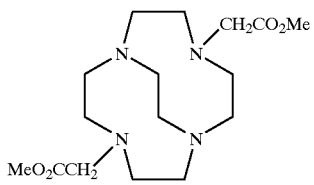

1.3.6.9

1.3.6.10 N,N',N''-Tris(carboxyethyl)-1,4,7-triazacyclononane

From 1,4,7-triazacyclononane (1.1.3), 3-chloropropionic acid and base.

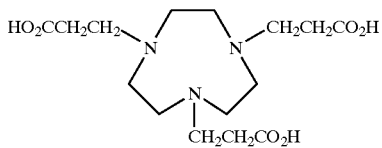

1.3.6.10

1.3.6.11 4,10-Bis(ethoxycarboxymethyl)-1,4,7,10-tetraazabicyclo[5.5.2]tetradecane From 1,4,7,10-tetraazabicyclo[5.5.2]tetradecane (1.1.20) and ethyl acrylate.

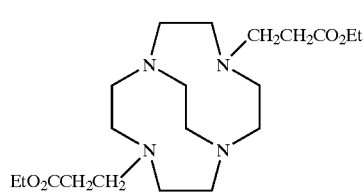

1.3.6.11

1.3.6.12 4,10-Bis(carboxymethyl)-1,4,7,10-tetraazabicyclo[5.5.2]tetradecane

From 1.3.6.11 by acid hydrolysis.

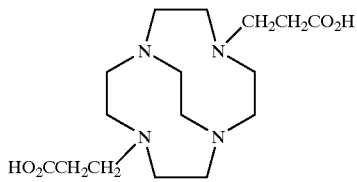

1.3.6.12

1.3.6.13 N,N',N''-Tris(ethoxycarbonylmethyl)-1,4,7-triazacyclononane

From 1,4,7-triazacyclononane (1.1.3), ethyl bromoacetate and base.

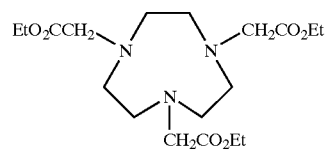

1.3.6.13

1.3.6.14 1,2-Bis-(4,7-methoxycarbonylmethyl-1,4,7-triazacyclononan-1-yl)-ethane From 1,2-bis-(4,7-carboxymethyl-1,4,7-Triazacyclononan-1-yl)ethane (1.3.6.7), MeOH/$SOCl_2$.

1.3.6.14

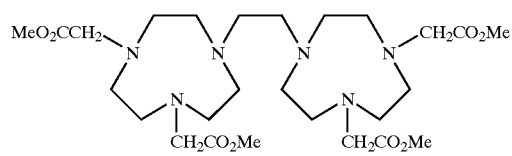

1.3.7 Synthesis of Polyaza Ligands with Pendant Arms Containing Aldehyde or Ketone Groups

1.3.7.1 N,N',N''-Tris(2,2-dimethoxyethyl)-1,4,7-triazacyclononane

From 1,4,7-triazacyclononane (1.1.3), 1-chloro-2,2-dimethoxyethane (commercially available) and sodium carbonate.

1.3.7.1

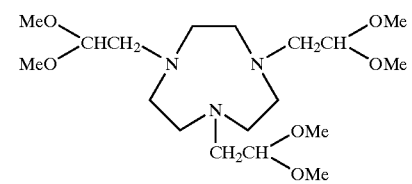

1.3.7.2 N,N',N''-Tris-(3,3-dimethyl-2-oxo-butyl)-1,4,7-triazacyclononane

From 1,4,7-triazacyclononane (1.1.3), bromomethyl t-butyl ketone (commercially available) and sodium carbonate.

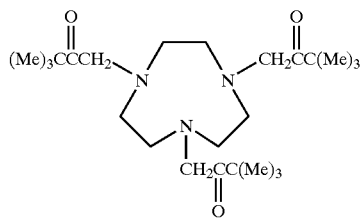

1.3.7.2

1.3.8 Synthesis of Polyaza Ligands with Pendant Arms Containing Pyrrole Groups

1.3.8.1 N,N',N''-Tris(-pyrrol-2-yl-methyl)-1,4,7-triazacyclononane

From 1,4,7-triazacyclononane (1.1.3), pyrrole-2-carboxaldehyde (commercially available) and $H_2/PtO_2$.

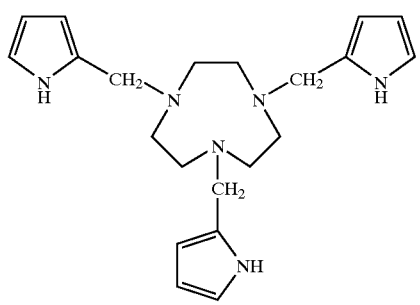

1.3.8.1

1.3.9 Synthesis of Polyaza Ligands with Pendant Arms Containing Amine Groups

1.3.9.1 N,N',N'-Tris(2-p-toluenesulfonyloxyethyl)-1,4,7-triazacyclononane

From 1,4,7-triazacyclononane (1.1.3), 2-(p-toluenesulfonylamino)-1-(p-toluenesulfonyloxy)ethane (1.1.16) and base.

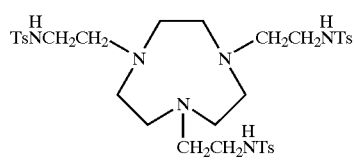

1.3.9.1

1.3.9.2 N,N',N''-Tris(2-aminoethyl)-1,4,7-triazacyclononane

From 1.3.9.1 and HBr/acetic acid.

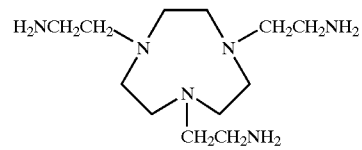

1.3.9.2

1.3.10 Synthesis of Polyaza Ligands with Pendant Arms Containing Amide Groups

1.3.10.1 N,N',N''-Tris(methylcarboxamide)-1,4,7-triazacyclononane

From N,N',N''-Tris-(methoxycarboxymethyl)-1,4,7-triazacyclononane (1.3.6.2) and ammonia.

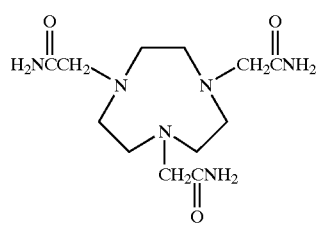

1.3.10.1

1.3.10.2 N,N',N''-Tris[-N-n-butyl (methylcarboxamide)]-1,4,7-triazacyclononane From N,N',N''-Tris-(methoxycarboxymethyl)-1,4,7-triazacyclononane (1.3.6.2) and butylamine.

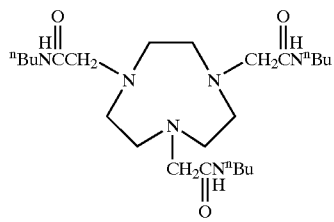

1.3.10.2

1.3.10.3 N,N',N''-Tris[-N-n-phenyl (methylcarboxamide)]-1,4,7-triazacyclononane From 1,4,7-triazacyclononane (1.1.3), N-phenylchloroacetamide (prepared from aniline and chloroacetyl chloride) and excess sodium carbonate.

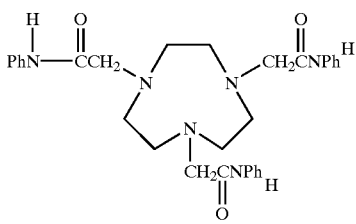

1.3.10.3

1.3.11 Synthesis of Polyaza Ligands with Pendant Arms Containing Phenolic Groups

1.3.11.1 4,7-Di-(2-hydroxy-benzyl)-1,4,7,10-tetraazabicyclo[5.5.2]tetradecane From 1,4,7,10-tetraazabicyclo[5.5.2]tetradecane (1.1.20), salicylaldehyde (excess) and $H_2/PtO_2$.

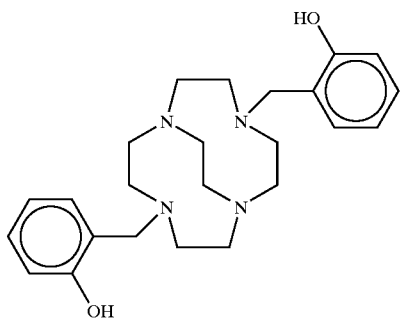

1.3.11.1

1.3.11.2 4-(2-hydroxy-benzyl)-1,4,7,10-tetraazabicyclo[5.5.2]tetradecane

From 1,4,7,10-tetrazabicyclo[5.5.2]tetradecane (1.1.20), salicylaldehyde (1.5 equivalents) and $H_2/PtO_2$.

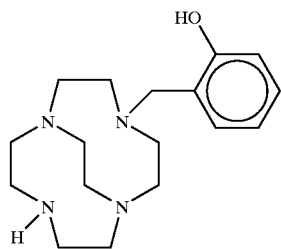

1.3.11.2

1.3.11.3 Bis-(2,2'-dihydroxybiphenylmethylene) ethylene diamine

From ethylenediamine (1.1.0) and 2,2'-dihydroxy benzophenone (commercially available) with removal of $H_2O$.

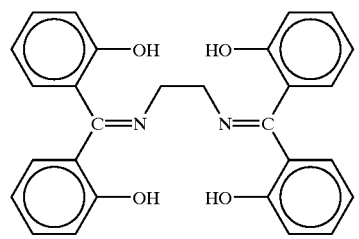

1.3.11.3

1.3.11.4 N,N'-Bis-(2,2'-dihydroxybiphenylmethyl) ethylene diamine

From 1.3.11.3 and sodium borohydride.

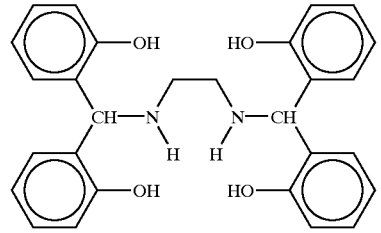

1.3.11.4

1.3.11.5 Bis-(2,4-dihydroxybiphenylmethylene) ethylenediamine

From ethylenediamine (1.1.0) and 2,4-dihydroxy benzophenone (commercially available) with removal of $H_2O$.

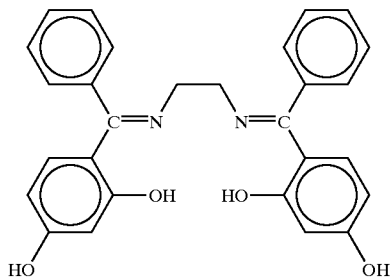

1.3.11.5

1.3.11.6 N,N'-Bis-(2,4-dihydroxybiphenylmethyl) ethylenediamine

From 1.3.11.5 and sodium borohydride.

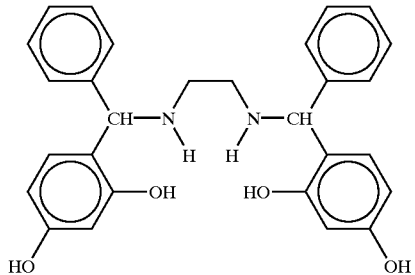

1.3.11.6

1.3.11.7 N,N"-Bis-(2,2'-dihydroxybiphenylmethylene)diethylene triamine

From diethylene triamine (1.1.1) and 2,2'-dihydroxy benzophenone with removal of $H_2O$.

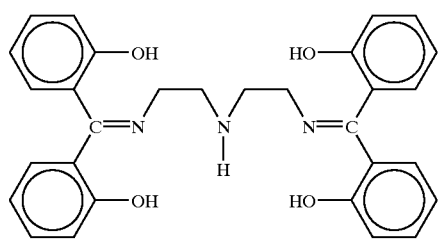

1.3.11.7

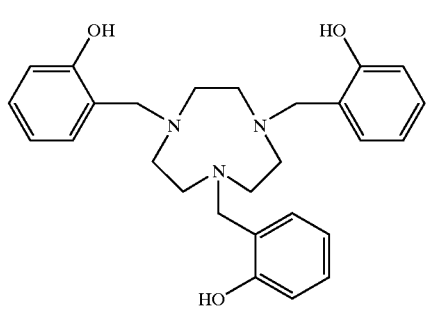

1.3.11.11

1.3.11.8 N,N''-Bis-(2,2'-dihydroxybiphenylmethyl) diethylene triamine

From 1.3.11.7 and sodium borohydride.

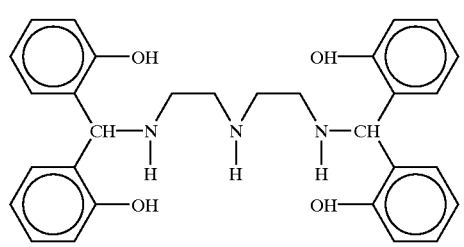

1.3.11.8

1.3.11.9 Bis-(2,2'-dihydroxybiphenylmethylene)-1,3-diaminopropane

From diaminopropane and 2,2'-dihydroxy benzophenone with removal of $H_2O$.

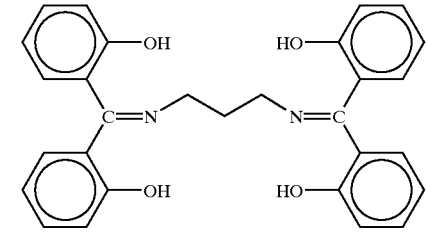

1.3.11.9

1.3.11.10 N,N'-Bis-(2,2'-dihydroxybiphenylmethyl)-1,3-diaminopropane

From and 1.3.11.9 and sodium borohydride.

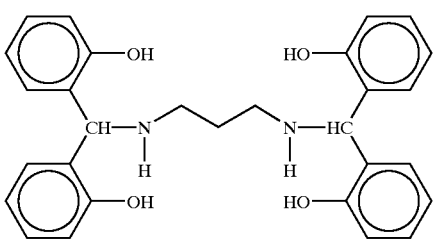

1.3.11.10

1.3.11.11 N,N',N''-Tris(2-hydroxybenzyl)-1,4,7-triazacyclononane

From 1,4,7-triazacyclononane, salicylaldehyde and $H_2/PtO_2$.

1.3.12 Synthesis of Polyaza Ligands with More Than One Species of Pendant Arm

1.3.12.1 N-(p-Toluenesulfonyl)-N',N''-bis(diethylphosphorylmethyl)-1,4,7-triazacyclononane From N-(p-toluenesulfonyl)-1,4,7-triazacyclononane dihydrobromide (1.3.13.31), formaldehyde and diethyl phosphite.

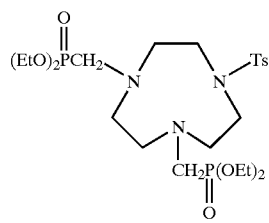

1.3.12.1

1.3.12.2 N,N'-Bis(diethylphosphorylmethyl)-1,4,7-triazacyclononane

From 1,4,7-triazacyclononane (1.1.3) trihydrobromide, one equivalent formaldehyde and one equivalent of diethyl phosphite. Purification of product by chromatography.

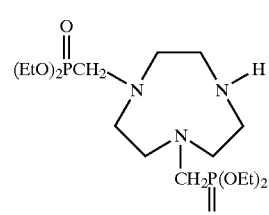

1.3.12.2

1.3.12.3 N,N'-Bis(dihydroxyphosphorylmethyl)-1,4,7-triazacyclononane

From 1.3.12.2 and HCl.

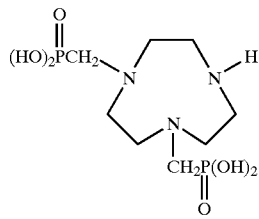
1.3.12.3

1.3.12.4 N-(Carboxymethyl)-N,N'-bis(dihydroxyphosphorylmethyl)-1,4,7-triazacyclononane From 1.3.12.3, chloroacetic and NaOH.

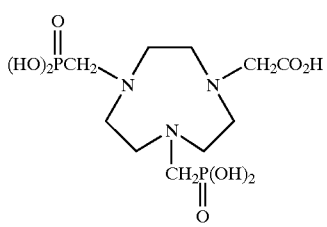
1.3.12.4

1.3.12.5 4-(2-Hydroxy-benzyl)-7-diethylphosphorylethyl-1,4,7,10-tetraazabicyclo[5.5.2]tetradecane From 4-(2-hydroxybenzyl)-1,4,7,10-tetraazabicyclo[5.5.2]tetradecane (1.3.11.2), diethyl phosphite and formaldehyde solution.

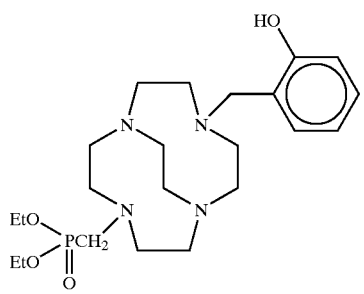
1.3.12.5

1.3.12.6 4-(2-hydroxy-benzyl)-7-phosphorylethyl-1,4,7,10-tetraazabicyclo[5.5.2]tetradecane From 1.3.12.5 and HCl.

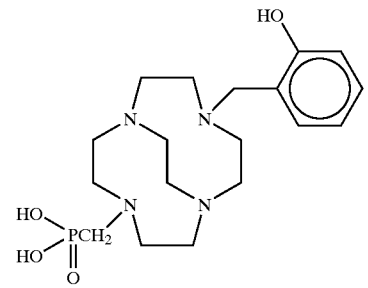
1.3.12.6

1.3.13 Miscellaneous Substituted Polyaza Compounds

1.3.13.1 1,2-Bis-(4,7-benzyloxycarbonyl-1,4,7-triazacyclononan-1-yl)ethane

From 1,2-bis-(1,4,7-triazacyclononan-1-yl)ethane(1.1.28) polyhydrobromide, potassium carbonate and benzyl chloroformate.

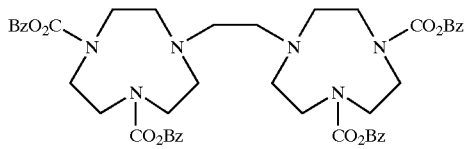
1.3.13.1

1.3.13.2 N-(p-Toluenesulfonyl)-N',N''-Bis-(benzyloxycarbonyl)-1,4,7-triazacyclononane From N-(p-toluenesulfonyl)-1,4,7-triazacyclononane dihydrobromide (1.3.13.31), $K_2CO_3$ and benzyl chloroformate.

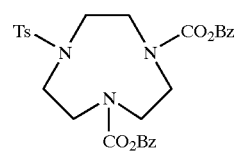
1.3.13.2

1.3.13.3 N-(p-Toluenesulfonyl)-N''-benzyloxycarbonyl-1,4,7-triazacyclononane From N-(p-toluenesulfonyl)-N',N''-bis(benzyloxycarbonyl)-1,4,7-triazacyclononane (1.3.13.2) and trimethylsilyl iodide.

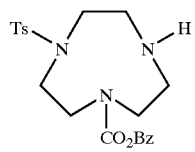
1.3.13.3

1.3.13.4 1,2-Bis[(1-p-toluenesulfonyl)-4-benzyloxycarbonyl-1,4,7-triazacyclonon-7-yl]ethane From 1-(p-toluenesulfonyl)-4-benzyloxycarbonyl-1,4,7-triazacyclononane (1.3.13.3), potassium carbonate and dibromoethane.

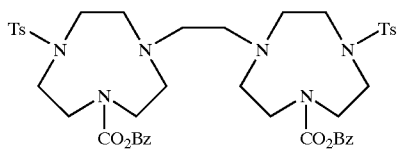

1.3.13.4

1.3.13.5 N,N',N"-Tris(phenylacetyl)-1,4,7-triazacyclononane

From 1,4,7-triazacyclononane (1.1.3), diethyl phenylacetylphosphonate [PhCH$_2$COP(O)(OEt)$_2$].

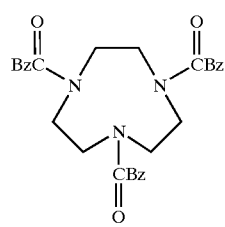

1.3.13.5

1.3.13.6 N,N',N"-Tris(2,3-Epoxypropyl-1,4,7-Triazacyclononane

From 1,4,7-triazacyclononane (1.1.3) and epibromohydrin.

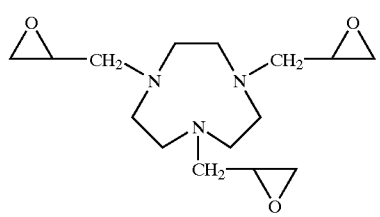

1.3.13.6

1.3.13.7 N,N',N"-Tri-allyl-1,4,7-triazacyclononane

From 1,4,7-triazacyclononane (1.1.3), sodium hydride and allyl bromide.

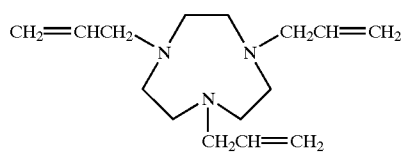

1.3.13.7

1.3.13.8 N,N',N"-Tris(benzyloxycarbonyl)-1,4,7-triazacyclononane

From 1,4,7-triazacyclononane (1.1.3), benzyl chloroformate and sodium carbonate.

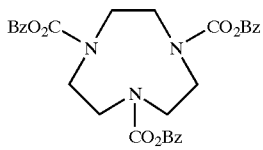

1.3.13.8

1.3.13.9 N,N'-Bis(benzyloxycarbonyl)-1,4,7-triazacyclononane

From N,N',N"-tris(benzyloxycarbonyl)-1,4,7-triazacyclononane (1.3.13.8) and iodotrimethylsilane.

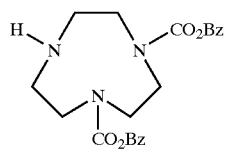

1.3.13.9

1.3.13.10 N,N'-Bis(benzyloxycarbonyl)-N"-(2-bromoethyl)-1,4,7-triazacyclononane From N,N'-bis(benzyloxycarbonyl)-1,4,7-triazacyclononane (1.3.13.9), dibromoethane and potassium carbonate.

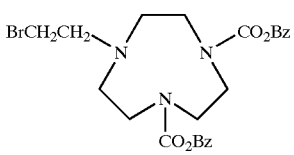

1.3.13.10

1.3.13.11 N-p-Toluenesulfonyl-N',N"-ditrifluoroacetyl-1,4,7-triazacyclononane From N-p-toluenesulfonyl-1,4,7-triazacyclononane (1.3.13.31), potassium carbonate and trifluoroacetic anhydride.

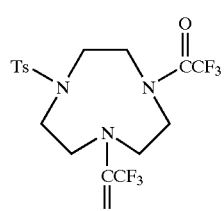

1.3.13.11

1.3.13.12 N-p-Toluenesulfonyl-N'-benzyl-1,4,7-triazacyclononane

From N-(p-toluenesulfonyl-1,4,7-triazacyclononane (1.3.13.31), sodium hydride and benzyl bromide.

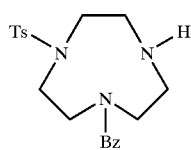

1.3.13.12

1.3.13.13 N-p-Toluenesulfonyl-N',N''-dibenzyl-1,4,7-triazacyclononane

From N-(p-toluenesulfonyl-1,4,7-triazacyclononane (1.3.13.31), sodium hydride and benzyl bromide.

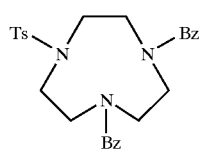

1.3.13.13

1.3.13.14 1,2-Bis(N-p-toluenesulfonyl-N'-benzyl)-1,4,7-triazacyclononan-1-yl)ethane From N-p-toluenesulfonyl-N'-benzyl-1,4,7-triazacyclononane (1.3.13.12), dibromoethane and potassium carbonate.

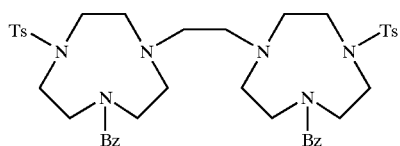

1.3.13.14

1.3.13.15 1,2-Bis(N,N'-ditrityl-1,4,7-triazacyclononan-1-yl)ethane

From 1,2-Bis(1,4,7-triazacyclononane)ethane (1.1.28), potassium carbonate and trityl chloride.

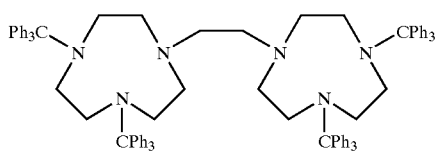

1.3.13.15

1.3.13.16 Spiro [4,8]-4,7-di-p-toluenesulfonyl-4,7-diaza-1-azotridecane halide From 1,4,7-triazacyclononane-N,N'-di-p-toluenesulfonyl hydrobromide (1.3.13.32), diiodobutane and potassium carbonate.

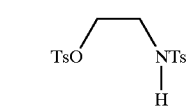

1.3.13.16

1.3.13.17 Tetrakis(p-toluenesulfonyl)-1,4,7,10-tetraazacyclotetradecane

From N,N',N''-tris(p-toluenesulfonyl)diethylenetriamine (1.3.13.18), potassium carbonate and bis(2-p-toluenesulfonyloxyethyl)-N-(p-toluenesulfonyl) amine (1.3.13.19).

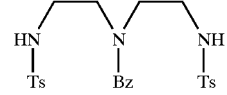

1.3.13.18

1.3.13.19

1.3.13.17

1.3.13.20 1,7-Bis(p-toluenesulfonyl)-4-benzyl-1,4,7-triazaheptane

From benzylamine, (2-p-toluenesulfonyoxyl)-N-(p-toluenesulfonyl)-ethylamine (1.3.13.21) and potassium carbonate.

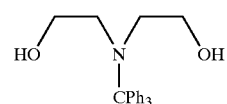

1.3.13.21

1.3.13.20

1.3.13.22 N-Tritylidiethanolamine

From diethanolamine and trityl chloride.

1.3.13.22

1.3.13.23 N-Trityl-bis(2-p-toluenesulfonyloxyethyl)amine

From N-trityldiethanolamine and p-toluenesulfonyl chloride.

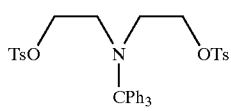

1.3.13.23

1.3.13.24 1,7-di-(p-toluenesulfonyl)-4-benzyl-10-trityl-1,4,7,10-tetraazacyclotetradecane From 1,7-di-p-toluenesulfonyl-4-benzyl-1,4,7-triazaheptane (1.3.13.20), sodium hydride and N-trityl-di-p-toluenesulfonyldiethanolamine (1.3.13.23).

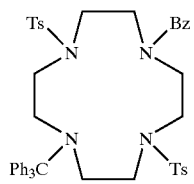

1.3.13.24

1.3.13.25 1,7-Di-(p-toluenesulfonyl)-1,4,7,10-tetraazacyclotetradecane

From 1,7-di-(p-toluenesulfonyl)-4-benzyl-10-trityl-1,4,7,10-tetraazacyclotetradecane (1.3.13.24) reduced by $H_2$ and Pd/C.

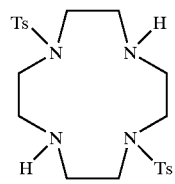

1.3.13.25

1.3.13.26 1,7-Di-(p-toluenesulfonyl)-4-benzyl-1,4,7,10-tetraazacyclotetradecane From reduction of 1.3.13.24.

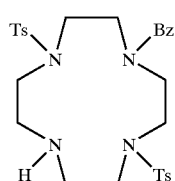

1.3.13.26

1.3.13.27 1,2-Bis-(4,10-di-p-toluenesulfonyl-7-benzyl-1,4,7,10-tetraazacyclotetradecan-1-yl)ethane From 1.3.13.26 and dibromoethane.

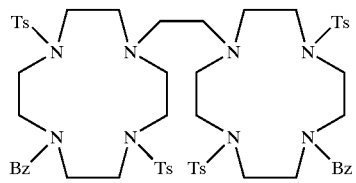

1.3.13.27

1.3.13.28 1,5,9,13-Tetraazatetracyclo[6,6,2,0$^{1,15}$,0$^{8,16}$]hexadecane From 1.1.6 and glyoxaldehyde.

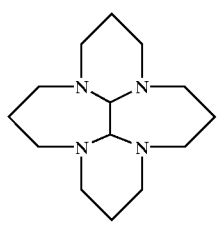

1.3.13.28

1.3.13.29 4,7-Diallyl-1,4,7-triazabicyclo[7,4,0]tridecane

From 1,4,7-triazabicyclo[7,4,0]tridecane trihydrobromide (1.1.14), sodium hydride and allyl bromide.

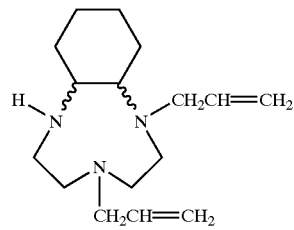

1.3.13.29

1.3.13.30 N-p-Toluenesulfonyl-1,4,7-triazacyclononane dihydrobromide

From N,N',N"-Tris(p-toluenesulfonyl)-1,4,7-triazacyclononane (1.3.13.31) prepared from 1.3.13.18, dibromoethane and base) and HBr/acetic acid.

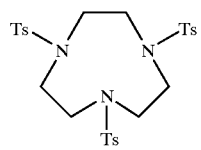

1.3.13.31

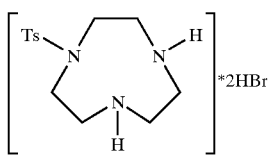

1.3.13.30

1.3.13.32 N,N'-Di-p-Toluenesulfonyl-1,4,7-triazacyclononane hydrobromide a) From N,N',N"-tris(p-toluenesulfonyl)-1,4,7-triazacyclononane (1.3.13.31 and HBr/acetic acid as the hydrobromide salt.

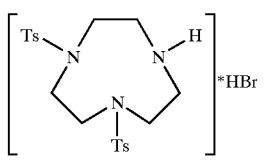

1.3.13.32

1.3.13.33 N,N,N',N'-Tetraallylethylenediamine

From ethylenediamine, sodium carbonate and allyl bromide.

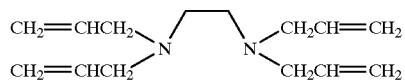

1.3.13.33

1.3.13.34 4,7,13-Tris(p-toluenesulfonyl)-1,4,7,10-13-pentaazabicyclo[8.5.2]heptadecane From 1,4,7,10,13-pentaazabicyclo[8.5.2]heptadecane (1.1.26), potassium carbonate and p-toluenesulfonyl chloride.

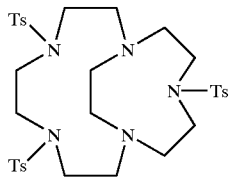

1.3.13.34

1.3.13.35 1,2-Bis(4-p-toluenesulfonyl-1,4,7-triazacyclonon-1-yl)ethane

From 1,2-bis(4,7-di-p-toluenesulfonyl-1,4,7-triazacyclonon-1-yl)ethane (1.1.30) and sulphuric acid.

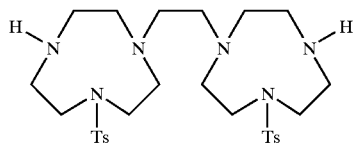

1.3.13.35

1.3.13.36 N,N'-(Di-p-toluenesulfonyl)-N"-benzyl-1,4,7-Triazacyclononane a) From N,N"-(p-toluenesulfonyl)-4-benzyl diethylenetriamine (1.3.13.20), sodium hydride and ethylene glycol di-p-toluenesulfonate (1.1.12).

b) From N,N'-bis(p-toluenesulfonyl)-1,4,7-triazacyclononane (1.3.13.32), sodium hydride and benzyl bromide.

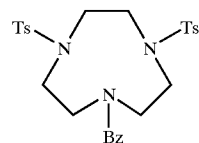

1.3.13.36

1.3.13.37 N-(p-Toluenesulfonyl)-N'-trityl-1,4,7-triazacyclononane

From N-(p-toluenesulfonyl-1,4,7-triazacyclononane dihydrobromide (1.3.13.30), sodium hydride and trityl chloride.

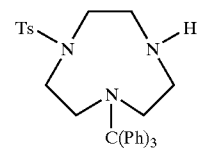

1.3.13.37

1.3.13.38 Hexakis(allyl) triethylenetetramine

From triethylenetetramine (1.1.2), sodium carbonate and allyl bromide.

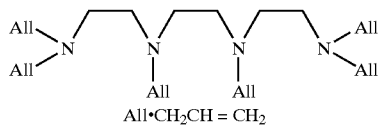

1.3.13.38

1.3.13.39 4,7-diallyl-1,4,7,10-tetraazabicyclo[5.5.2]tetradecane

From 1,4,7,10-tetraazabicyclo[5.5.2]tetradecane (1.1.4), allyl bromide and base.

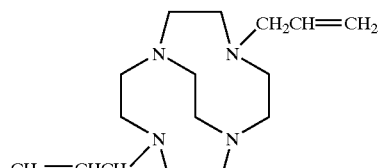

1.3.13.39

Example 2

This example illustrates the preparation of metal complexes using the chelating agents (ligands) described in Example 1.

2.1 Synthesis of Metal Complexes

Water soluble salts of metals and compounds described in the above examples were heated in water or alcohol solvents followed by base addition to neutral or basic pH. Alternately, an excess of these metals in the form of their corresponding insoluble oxides or hydroxides was heated with the acid form of the compounds described in preceding sections until complexation was complete, followed by filtration to remove uncomplexed excess metal oxide or hydroxide. In either case complex formation was verified by chromatography. Employing these methods the following complexes were synthesized:

2.1.1 Iron (III) complexes with the following Compounds:
2.1.1.1. 1,2-Bis(1,4,7-triazabicyclononan-1-yl)ethane (1.1.29)
2.1.1.2. N,N',N''-Tris(2-hydroxy-3-isopropoxypropyl)-1,4,7-triazacyclononane (1.3.1.1)
2.1.1.3. (R, R, R) N,N',N''-Tris(2-hydroxy-3-isopropoxypropyl)-1,4,7-triazacyclononane (1.3.1.2).
2.1.1.4. (S, S, S) N,N',N''-Tris(2-hydroxy-3-isopropoxypropyl)-1,4,7-triazacyclononane (1.3.1.3).
2.1.1.5. N,N',N''-Tris(2-hydroxy-3-isobutoxypropyl)-1,4,7-triazacyclononane (1.3.1.4).
2.1.1.6. (R, R, R) N,N',N''-Tris(2-hydroxy-3-isobutoxypropyl)-1,4,7-triazacyclononane (1.3.1.5).
2.1.1.7. N,N',N''-Tris(2-hydroxy-3-methoxypropyl)-1,4,7-triazacyclononane (1.3.1.6).
2.1.1.8. N,N',N''-Tris(2,3-dihydroxypropyl)-1,4,7-triazacyclononane (1.3.1.7).
2.1.1.9. N,N',N''-Tris(2-hydroxy-3-allyloxypropyl)-1,4,7-triazacyclononane (1.3.1.9).
2.1.1.10. N,N',N''-Tris(2-hydroxy-3-phenoxypropyl)-1,4,7-triazacyclononane (1.3.1.10).
2.1.1.11. N,N',N''-Tris(2-hydroxy-2,2-diethoxymethylene)ethyl-1,4,7-triazacyclononane (1.3.1.11).
2.1.1.12. N,N',N''-Tris(2-hydroxy-2,2-dimethoxymethyl)ethyl-1,4,7-triazacyclononane (1.3.1.12).
2.1.1.13. N,N',N''-Tris(2-hydroxy-2,2-diisopropyloxymethyl)ethyl-1,4,7-triazacyclononane (1.3.1.13).
2.1.1.14. N,N',N''-Tris[2-hydroxy-bis(2-furfurylmethyl)ethyl]-1,4,7-triazacyclononane (1.3.1.14).
2.1.1.15. N,N',N''-Tris(3-hydroxy-1,5-dioxacycloheptyl-3-methyl)-1,4,7-triazacyclononane (1.3.1.15).
2.1.1.16. N,N',N''-Tris[(3-Hydroxy-7,7-dimethyl-1,5-dioxacyclooct-3-yl)-methyl ]-1,4,7-triazacyclononane (1.3.1.16).
2.1.1.17. N,N',N'-Tris[(3-hydroxy-7-methyl-1,5-dioxacyclohept-3-yl)methyl]-1,4,7-triazacyclononane (1.3.1.17).
2.1.1.18. N,N',N''-Tris[(3-hydroxy-6,6,7,7-tetramethyl-1,5-dioxacyclohept-3-yl)methyl]-1,4,7-Triazacyclononane (1.3.1.18).
2.1.1.19. N,N',N''-Tris[(3-hydroxy-benzo[b]-1,5-dioxacycloheptyl)methyl]1,4,7-triazacyclononane (1.3.1.19).
2.1.1.20. N,N',N'-Tris[(3-hydroxy-1,5-dioxacyclooctan-3-yl)methyl]-1,4,7-triazacyclononane (1.3.1.20).
2.1.1.21. N,N',N''-Tris[(4-fluoro-2-hydroxy-3-isopropyl-4-methyl)pentyl]-1,4,7- triazacyclononane (1.3.1.22).
2.1.1.22. N,N',N''-Tris-[2-hydroxy-3-(1-fluoroethyl)-4-hydroxypentyl]-1,4,7-triazacyclononane (1.3.1.23).
2.1.1.23. N,N',N''-Tris[2-hydroxy-2-(1-fluoroethyl)-2-(1-methoxyethyl)ethyl]-1,4,7-triazacyclononane (1.3.1.24).
2.1.1.24. N,N',N''-Tris(2-hydroxy-2-ethyl-3-methoxybutyl)-1,4,7-triazacyclononane (1.3.1.25).
2.1.1.25. N,N',N''-Tris[(2,3-dihydroxy-2-ethyl)butyl]-1,4,7-triazacyclononane (1.3.1.26).
2.1.1.26. N,N',N''-Tris[2-hydroxy-2,2-bis(1-fluoroethyl)ethyl]-1,4,7-triazacyclononane (1.3.1.27).
2.1.1.27. N,N',N''-Tris[2-hydroxy-2,2-bis(1-methoxyethyl)ethyl]-1,4,7-triazacyclononane (1.3.1.28).
2.1.1.28. N,N',N''-Tris[(3,3-dimethyl-2-hydroxy)butyl]-1,4,7-triazacyclononane (1.3.1.29).
2.1.1.29. N,N',N''-Tris(2-hydroxycyclohexan-1-yl)-1,4,7-triazacyclononane (1.3.1.33).
2.1.1.30. N,N',N'',N'''-Tetrakis(2,3-dihydroxypropyl)-1,4,7,10-tetraazacyclotetradecane (1.3.1.38).
2.1.1.31. 4,10-Bis(2-hydroxypropyl)-1,4,7,10-tetraazabicyclo[5.5.2]tetradecane (1.3.1.39).
2.1.1.32. 4,10-Bis-(2-hydroxyethyl)-1,4,7,10-tetrazabicyclo[5.5.2]tetradecane (1.3.1.40).
2.1.1.33. 4,10-Bis-(2,3-dihydroxypropyl)-1,4,7,10-tetraazabicyclo[5.5.2]tetradecane (1.3.1.42).
2.1.1.34. N,N',N''-Tris[(2,4-dihydroxy-3-isopropyl-4-methyl)pentyl]-1,4,7-triazacyclononane (1.3.1.54).
2.1.1.35. N,N',N'-Tris(2-hydroxy-bis(2,2-dihydroxymethyl)ethyl]-1,4,7-triazacyclononane (1.3.1.55).
2.1.1.36. N,N',N''-Tris(dihydroxyphosphoryl mono butyl ester)methyl-1,4,7-triazacyclononane (1.3.2.2).
2.1.1.37. N,N',N''-Tris(dihydroxyphosphorylmethyl monoethyl ester)-1,4,7-triazacyclononane (1.3.2.4).
2.1.1.38. N,N',N''-Tris(dihydroxyphosphorylmethyl monooctyl ester)-1,4,7-triazacyclononane (1.3.2.6).
2.1.1.39. N,N',N''-Tris(dihydroxyphosphorylmethyl monoisobutyl ester)-1,4,7-triazacyclononane (1.3.2.8).
2.1.1.40. 1,2-Bis(N,N'-bis(dihydroxyphosphorylmethyl)-1,4,7-triazacyclononan-1-yl)ethane (1.3.3.1).
2.1.1.41. 1,2-Bis(N,N'-bis(dihydroxyphosphorylmethyl)-1,4,7-triazacyclononan-1-yl)propane (1.3.3.2).
2.1.1.42. 4,10-Bis(dihydroxyphosphorylmethyl)-1,4,7,10-tetraazabicyclo[5.5.2]tetradecane.
2.1.1.43. 4,7,13-Tris(dihydroxyphosphorylmethyl)-1,4,7,10,13-pentaazabicyclo[8.5.2]heptadecane (1.3.3.4).
2.1.1.44. N,N',N''-Tris(dihydroxyphosphorylethyl)-1,4,7-triazacyclononane (1.3.3.5).
2.1.1.45. N',N'',N''',N''''-Tetrakis(dihydroxyphosphorylethyl)-1,4,7,10-tetraazacyclododecane (1.3.3.6).
2.1.1.46. 4,10-Bis(dihydroxyphosphorylethyl)-1,4,7,10-tetraazabicyclo[5.5.2]tetradecane (1.3.3.7).
2.1.1.47. N,N',N''-Tris[(N-methyl-N-hydroxycarbamoyl)methyl]-1,4,7-triazacyclononane (1.3.5.2).
2.1.1.48. N,N',N''-Tris[(N-isopropyl-N-hydroxycarbamoyl)methyl]-1,4,7-triazacyclononane (1.3.5.4).
2.1.1.49. N,N',N''-Tris[(N-t-butyl-N-hydroxycarbamoyl)methyl]-1,4,7-triazacyclononane (1.3.5.6).
2.1.1.50. N,N',N''-Tris[(N-hydroxycarbamoyl)methyl]-1,4,7-triazacyclononane (1.3.5.8).
2.1.1.51. N,N',N''-Tris[(N-methoxycarbamoyl)methyl]-1,4,7-triazacyclononane (1.3.5.9).
2.1.1.52. 4,10-Bis[(N-hydroxy-N-methylcarbamoyl)methyl]-1,4,7,10-tetraazabicyclo[5.5.2]tetradecane (1.3.5.11).
2.1.1.53. N,N',N''-Tris[(1-hydroxy-2-pyrrolidon-5-yl)methyl]-1,4,7-triazacyclononane (1.3.5.13).
2.1.1.54. N,N',N''-Tris[(1-hydroxy-2-pyrrolidon-5-yl)methyl]-1,4,7-triazacyclononane (1.3.5.13).
2.1.1.55. N,N',N''-Tris(carboxymethyl)-1,4,7-triazacyclononane (1.3.6.1).
2.1.1.56. 1,2-Bis-(4,7-carboxymethyl-1,4,7-triazacyclononan-1-yl)ethane (1.3.6.7).
2.1.1.57. N,N',N''-Tris(carboxyethyl)-1,4,7-triazacyclononane (1.3.6.10).
2.1.1.58. 4,10-Bis(carboxymethyl)-1,4,7,10-tetraazabicyclo[5.5.2]tetradecane (1.3.6.12).
2.1.1.59. N,N',N''-Tris(2,2-dimethoxyethyl)-1,4,7-triazacyclononane (1.3.7.1).
2.1.1.60. N,N',N''-Tris(pyrrol-2-yl-methyl)-1,4,7-triazacyclononane (1.3.8.1).
2.1.1.61. N,N',N''-Tris[N-n-butyl(carbamoylmethyl)]-1,4,7-triazacyclononane (1.3.10.2).
2.1.1.62. N,N',N''-Tris[N-phenyl(carbamoylmethyl)]-1,4,7-triazacyclononane (1.3.10.3).

2.1.1.63. 4,7-Bis(2-hydroxybenzyl)-1,4,7,10-tetraazabicyclo[5.5.2]tetradecane (1.3.11.1).
2.1.1.64. N,N'-Bis-(2,4-dihydroxybiphenylmethyl) ethylenediamine (1.3.11.6).
2.1.1.65. N,N'-Bis-(2,2'-dihydroxybiphenylmethyl) diethylenetriamine (1.3.11.8).
2.1.1.66. N,N'-Bis-(2,2'-dihydroxybiphenylmethyl)-1,3-diaminopropane (1.3.11.10).
2.1.1.67. N,N',N"-Tris(2-hydroxybenzyl)-1,4,7-triazacyclononane (1.3.11.11).
2.1.1.68. N,N'-bis(dihydroxyphosphorylmethyl)-1,4,7-Triazacyclononane (1.3.12.3).
2.1.1.69. N-(carboxymethyl)-N',N"-bis(dihydroxyphosphorylmethyl)-1,4,7-triazacyclononane (1.3.12.4).

2.1.2 Gadolinium (III) complexes with the following chelators:

2.1.2.1. 1,2-Bis(N,N'-bis(dihydroxyphosphorylmethyl)-1,4,7-triazacyclononan-1-yl)ethane (1.3.1.13).
2.1.2.2. 1,2-Bis(N,N'-bis(dihydroxyphosphrylmethyl)-1,4,7-triazacyclononan-1-yl)propane (1.3.3.2).
2.1.2.3. 4,7,13-Tris(dihydroxyphosphorylmethyl)-1,4,7,10,13-pentaazabicyclo[8.5.2]heptadecane (1.3.3.4).
2.1.2.4. N,N',N",N"'-Tetrakis(dihydroxyphosphorylethyl)-1,4,7,10-tetraazacyclododecane (1.3.3.6).
2.1.2.5. N,N',N"-Tris[2-dihydroxyphosphoryl-1-hydroxy)ethyl]-1,4,7-triazacyclononane (1.3.4.3).
2.1.2.6. 1,2-Bis-(4,7-carboxymethyl-1,4,7-triazacyclononan-1-yl)ethane (1.3.6.7).
2.1.2.7. N,N'-Bis-(2,2'-dihydroxybiphenylmethyl) ethylenediamine (1.3.11.4).
2.1.2.8. N,N'-Bis-(2,4-dihydroxybiphenylmethyl) ethylenediamine (1.3.11.6).

2.1.3 Copper (II) complexes with the following Compounds:

2.1.3.1. 1,4,7,10-Tetraazabicyclo[5.5.2]tetradecane (1.1.22).
2.1.3.2. N,N',N"-Tris(2-hydroxy-2,2-diisopropyloxymethyl) ethyl-1,4,7-triazacyclononane (1.3.1.13).
2.1.3.3. 4,10-Bis(2-Hydroxypropyl)-1,4,7,10-tetraazabicyclo[5.5.2]tetradecane (1.3.1.39).
2.1.3.4. 4,7-Bis(carboxymethyl)-1,4,7,10-tetraazabicyclo[5.5.2]tetradecane (1.3.6.8).
2.1.3.5. 4,10-Bis(carboxymethyl)-1,4,7,10-tetraazabicyclo[5.5.2]tetradecane (1.3.6.12).
2.1.3.6. 4,7-Bis(2-hydroxybenzyl)-1,4,7,10-tetraazabicyclo[5.5.2]tetradecane (1.3.11.1).

2.1.4 Zinc (II) complexes with the following Compounds:

2.1.4.1. N,N',N"-Tris(2-hydroxy-2,2-diisopropyloxymethyl) ethyl-1,4,7-triazacyclononane (1.3.1.13).
2.1.4.2. 4,7-Bis(carboxymethyl)-1,4,7,10-tetraazabicyclo[5.5.2]tetradecane (1.3.6.8).
2.1.4.3. 4,10-Bis(carboxymethyl)-1,4,7,10-tetraazabicyclo[5.5.2]tetradecane (1.3.6.12).
2.1.4.4. 4,7-Bis(2-hydroxybenzyl)-1,4,7,10-tetraazabicyclo[5.5.2]tetradecane (1.3.11.1).

2.1.5 Manganese (II) complexes with the following Compounds:

2.1.5.1. 4,10-Bis(dihydroxyphosphorylmethy)-1,4,7,10-tetraazabicyclo[5.5.2]tetradecane (1.3.3.3).
2.1.5.2. 4,7,13-Tris(dihydroxyphosphorylmethyl)-1,4,7,10,13-pentaazabicyclo[8.5.2]heptadecane (1.3.3.4).
2.1.5.3. 1,2-Bis-(4,7-carboxymethyl-1,4,7-triazacyclononan-1-yl)ethane (1.3.6.7).
2.1.5.4. 4,7-Bis(carboxymethyl)-1,4,7,10-tetraazabicyclo[5.5.2]tetradecane (1.3.6.8).

2.1.6 Cadmium (II) complexes with the following Compounds:

2.1.6.1 4,7,13-Tris(dihydroxyphosphorylmethyl)-1,4,7,10,13-pentaazabicyclo[8.5.2]heptadecane (1.3.3.4).

2.1.7 Lead (II) complexes with the following Compounds:

2.1.7 4,7,13-Tris(dihydroxyphosphorylmethyl)-1,4,7,10,13-pentaazabicyclo[8.5.2]heptadecane (1.3.3.4).

2.1.8 Mercury (II) complexes with the following Compounds:

2.1.8.1 4,7,13-Tris(dihydroxyphosphorylmethyl)-1,4,7,10,13-pentaazabicyclo[8.5.2]heptadecane (1.3.3.4).

2.1.9 Nickel (II) complexes with the following Compounds:

2.1.9.1 4,7-Bis(carboxymethyl)-1,4,7,10-tetraazabicyclo[5.5.2]tetradecane (1.3.6.8).

2.1.10 Calcium (II) complexes with the following Compounds:

2.1.10.1. 4,10-Bis(carboxymethyl)-1,4,7,10-tetraazabicyclo[5.5.2]tetradecane (1.3.6.12).
2.1.10.2. 4,7-Bis(2-hydroxybenzyl)-1,4,7,10-tetraazabicyclo[5.5.2]tetradecane (1.3.11.1).

2.1.11 Magnesium (II) complexes with the following Compounds:

2.1.11.1. 4,10-Bis(carboxymethyl)-1,4,7,10-tetraazabicyclo[5.5.2]tetradecane (1.3.6.12).
2.1.11.2. 4,7-Bis(2-hydroxybenzyl)-1,4,7,10-tetraazabicyclo[5.5.2]tetradecane (1.3.11.1).

2.2 Synthesis of Radioactive Complexes

Water soluble salts of radioisotopes of iron(III) and gadolinium or manganese (II) (e.g., chloride salts of Fe-59, Gd-153) and chelators described in Examples 1.3 were heated in water, alcohol or DMSO solvents followed by base addition to achieve neutral or basic pH. Complex formation was verified by radiochromatography. Employing this method the following complexes were synthesized.

2.2.1 Complexes of Fe-59

2.2.1.1. N,N',N"-Tris(2-hydroxy-3-isopropoxypropyl)-1,4,7-triazacyclononane (1.3.1.1).
2.2.1.2. (R, R, R) N,N',N"-Tris(2-hydroxy-3-isopropoxypropyl)-1,4,7-triazacyclononane (1.3.1.2).
2.2.1.3. (S, S, S) N,N',N"-Tris(2-hydroxy-3-isopropoxypropyl)-1,4,7-triazacyclononane (1.3.1.3).
2.2.1.4. (R, R, R) N,N',N"-Tris(2-hydroxy-3-isobutoxypropyl)-1,4,7-triazacyclononane (1.3.1.5).
2.2.1.5. N,N',N"-Tris(2-hydroxy-3-methoxypropyl)-1,4,7-triazacyclononane (1.3.1.6).
2.2.1.6. N,N',N"-Tris(2,3-dihydroxypropyl)-1,4,7-triazacyclononane (1.3.1.7).
2.2.1.7. N,N',N"-Tris(2-hydroxy-2,2-diisopropyloxymethyl) ethyl-1,4,7-triazacyclononane (1.3.1.13).

2.2.1.8. N,N',N"-Tris(3-hydroxy-1,5-dioxacycloheptyl-3-methyl)-1,4,7-triazacyclononane (1.3.1.15).

2.2.1.9. N,N',N"-Tris[(3-hydroxy-7,7-dimethyl-1,5-dioxacyclooct-3-yl)-methyl]-1,4,7-triazacyclononane (1.3.1.16).

2.2.1.10. N,N',N"-Tris[(3-hydroxy-6,6,7,7-tetramethyl-1,5-dioxacyclohept-3-yl)methyl]-1,4,7-triazacyclononane (1.3.1.18).

2.2.1.11. N,N',N"-Tris[(3-hydroxy-1,5-dioxacyclooctane-3-yl)methyl]-1,4,7-triazacyclononane (1.3.1.20).

2.2.1.12. N,N',N"-Tris(2-hydroxy-2-methylpropyl)-1,4,7-triazacyclononane (1.3.1.21).

2.2.1.13. N,N',N"-Tris[(2,3-dihydroxy-2-ethylbutyl)]-1,4,7-triazacyclononane (1.3.1.26).

2.2.1.14. N,N',N"-Tris[2-hydroxy-2,2-bis(1-methoxyethyl) ethyl]-1,4,7-triazacyclononane (1.3.1.28).

2.2.1.15. N,N',N"-Tris(2-hydroxypropyl)-1,4,7-triazacyclononane (1.3.1.30).

2.2.1.16. N,N',N"-Tris(dihydroxyphosphorylmethyl monobutyl ester)-1,4,7-triazacyclononane (1.3.2.2).

2.2.1.17. N,N',N"-Tris(dihydroxyphosphorylmethyl monoethyl ester)-1,4,7-triazacyclononane (1.3.2.4).

2.2.1.18. 4,10-Bis(dihydroxyphosphorylmethyl)-1,4,7,10-tetraazabicyclo[5.5.2]tetradecane (1.3.3.3).

2.2.1.19. N,N',N"-Tris(dihydroxyphosphorylethyl)-1,4,7-triazacyclononane (1.3.3.5).

2.2.1.20. N,N',N",N"'-Tetrakis(dihydroxyphosphorylethyl)-1,4,7,10-tetraazacyclododecane (1.3.3.6).

2.2.1.21. 4,10-Bis(dihydroxyphosphorylethyl)-1,4,7,10-tetraazabicyclo[5.5.2]tetradecane (1.3.3.7).

2.2.1.22. N,N',N"-Tris{[(diethylphosphoryl)-α-hydroxy] ethyl}-1,4,7-triazacyclononane (1.3.4.2).

2.2.1.23. N,N',N"-Tris[(N-methyl-N-hydroxycarbamoyl) methyl]-1,4,7-triazacyclononane (1.3.5.2).

2.2.1.24. N,N',N"-Tris[(N-isopropyl-N-hydroxycarbamoyl) methyl]-1,4,7-triazacyclononane (1.3.5.4).

2.2.1.25. N,N',N"-Tris[(N-t-butyl-N-hydroxycarbamoyl) methyl]-1,4,7-triazacyclononane (1.3.5.6).

2.2.1.26. 1,2-Bis-(4,7-carboxymethyl-1,4,7-triazacyclononan-1-yl)ethane (1.3.6.7).

2.2.1.27. N,N',N"-Tris(carboxyethyl)-1,4,7-triazacyclononane (1.3.6.10).

2.2.1.28. N,N',N"-Tris[N-n-butyl(methylcarboxamide)]-1,4,7-triazacyclononane (1.3.10.2).

2.2.1.29. 4,7-Bis(2-hydroxybenzyl)-1,4,7,10-tetraazabicyclo[5.5.2]tetradecane (1.3.11.1).

2.2.1.30. N,N'-Bis(dihydroxyphosphorylmethyl)-1,4,7-triazacyclononane (1.3.12.3).

2.2.1.31. N-(carboxymethyl)-N',N"-bis(dihydroxyphosphorylmethyl)-1,4,7-triazacyclononane (1.3.12.4).

2.2.2 Complexes of Mn-54

2.2.2.1 4,7-Bis(carboxymethyl)-1,4,7,10-tetraazabicyclo[5.5.2]tetradecane (1.3.6.8).

Example 3

This example illustrates the ability of the chelating agents described above to inhibit cell replication in vitro.

3.1: Inhibition of Bacterial Replication

This example demonstrates the ability of a representative example of the claimed ligands to inhibit replication of various bacteria in vitro.

N,N',N"-tris(dihydroxyphosphorylmethyl)-1,4,7-triazacyclononane was prepared as described in Example 1C in U.S. Pat. No. 5,236,695. Studies were performed to determine its ability to inhibit bacterial growth. For *Streptococcus hemolyticus*, *Listeria monocytogenes*, *Enterobacter cloacae* and *Klebsiella pneumoniae* the minimum inhibitory concentration was determined to be 0.15 mM/L. For *Enterococcus fecalis*, *Pseudomonas aeruginosa* and *Acinobacter anitratus* the minimum inhibitory concentration was determined to be 0.3 mM/L.

3.2: Inhibition of Mycotic Cell Replication in vitro

This example demonstrates the ability of a representative example of the claimed ligands to inhibit mycotic (fungal) cell replication in vitro.

N,N',N"-tris(dihydroxyphosphorylmethyl)-1,4,7-triazacyclononane was prepared as described in Example 1C in U.S. Pat. No. 5,236,695. Studies were performed to determine its ability to inhibit growth of mycotic (fungal) organisms.

For *Microsporum canis* the minimum inhibitory concentration was 0.233 mM/L or less. For *Candida albicans* and *Trichophyton rubrum* the minimal inhibitory concentration was 2.33 mM/L. For *Trichophyton mentagrophytes*, *Trichophyton tonsuras* and *Trichophyton violaceum* the minimal inhibitory concentration was 23.3 mM/L.

3.3: Inhibition of Mammalian Cell Replication in vitro

This example demonstrates the ability of representative examples of the claimed ligands to inhibit mammalian cell replication in vitro.

N,N',N"-tris(dihydroxyphosphorylmethyl)-1,4,7-triazacyclononane was prepared as described in Example 1C in U.S. Pat. No. 5,236,695.

Concentrations of this ligand of 0.009 mM/L inhibited the growth of both BGM cells (a continuous cell line of monkey origin) and HFF cells (human foreskin fibroblasts).

N,N',N"-Tris(carboxymethyl)-1,4,7-Triazacyclononane (Example 1.3.6.1) at a concentration of 0.009 mM/L inhibited BGM cell growth and a concentration of 0.019 mM/L inhibited HFF cell growth.

N,N',N"-Tris(ethoxycarbonylmethyl)-1,4,7-Triazacyclononane (Example 1.3.6.13) at a concentration of 0.04 mM/L inhibited BGM cell growth and at a concentration of 0.16 mM/L inhibited HFF cell growth. Diethylene triamine penta acetic acid at a concentration of 0.075 mM/L inhibited BGM cell growth and at 0.3 mM/L inhibited HFF cell growth.

Example 4

This example demonstrates the relative lack of toxicity of a representative example of the claimed ligands toward nonproliferating mammalian cells in vitro.

N,N',N"-tris(dihydroxyphosphorylmethyl)-1,4,7- triazacyclononane was prepared as described in Example 1C in U.S. Pat. No. 5,236,695.

A concentration of 0.3 mM of this agent was added to mature, nonreplicating cultures of HFF (human foreskin fibroblasts) kept in maintenance media and no effect on the resting cells was observed over a five-day period of observation.

Example 5

This example illustrates the low in vivo toxicity of a representative ligand administer intravenously to mice.

Over 50% of mice receiving 4.0 mM/kg intravenously of the sodium salt of N,N',N"-tris- (dihydroxyphosphorylmethyl)-1,4,7-triazacyclononane (Example 1C in U.S. Pat. No. 5,236,695) as a single intravenous dose survived for over 14 days following such administration demonstrating that the acute LD50 of this agent is in excess of 4 mM/kg. This in vivo LD50 toxicity dose results in an instantaneous in vivo concentration which is orders of magnitude greater than the dose of this agent which inhibits mammalian cell replication in vitro (0.009 mM/L).

Example 6

This example demonstrates the relatively low subacute toxicity of a representative ligand administered intravenously in repeated doses to rats.

Ten male Sprague Dawley rats 29 days old and weighing between 73.4 and 87.8 grams at the beginning of the experiment were randomized, employing the block stratification method, into two groups consisting of five rats each. On each of days 1, 2, 3, 6, 7, 8, 9, 10, 13 and 14 of the experiment one set of rats received an intravenous dose of N,N',N"-tris(dihydroxyphosphorylmethyl)-1,4,7-triazacyclononane (Example 1 C in U.S. Pat. No. 5,236,695) equal to 0.05 millimoles per kg of initial body weight (experimental group) while the other group received an equivalent volume of normal saline solution. The weights of the animals were recorded three times per week and the animals were sacrificed on the 28th day, major organs removed and weighed and tissues removed for microscopic examination. There was no statistically significant difference in weight or rate of weight gain between the experimental and control group of rats, either during the period of injections or in the two-week post-injection period. There were no differences observed between the weights of major organs of the experimental vs. the control group. There were no differences between the tissues of the experimental vs. the control group upon microscopic examination of the tissues obtained at the time of necropsy.

Example 7

This example illustrates the in vivo distribution of radioisotopic complexes

Examples of the in vivo distribution of radioisotopic complexes of representative ligands are herein disclosed which demonstrate the ability of these agents to be predominantly excreted by the kidneys, or the liver, or to pass across cell membranes and accumulate in the intracellular fluid space (e.g. in heart muscle). Those skilled in the art will recognize that a similar in vivo distribution can be anticipated from non-radioisotopic paramagnetic complex species.

In the following examples certain radioisotopic complexes of the subject ligands were administered intravenously to mice and the tissue distribution of the radioisotopic complexes was measured by detection of radioisotopic content of tissues removed at necropsy.

6.1: Example of a Complex Which is Predominantly Excreted by the Kidneys in the Urine The iron-59 labeled complex of N,N',N'-tris(2,3-dihydroxy propyl)-1,4,7-triazacyclononane (Example 2.2.1.6) was administered intravenously to mice and at necropsy the tissue distribution of radioactivity showed predominant concentration of the agent in the kidneys and urine.

6.2: Example of a Complex Which is Predominantly Excreted by the liver in the Bile The iron-59 complex of N,N',N"- tris(2'-hydroxy-3-isopropoxypropyl)-1,4,7-triazacyclononane (Example 2.2.1.1) was administered intravenously to mice and at necropsy the tissue distribution of radioactivity showed predominant concentration of the agent in the liver, bile and intestinal contents.

6.3: Example of a Complex Which Rapidly Passes Accross Cell Membranes and Enters the Intracellular Fluid Space The iron-59 complex of N,N',N"-tris[2-hydroxy-(2,2-diisopropyloxymethyl)ethyl]-1,4,7-triazacyclononane (Example 2.2.1.7) was administered intravenously to mice and at necropsy the tissue distribution of activity was consistent with an intracellular as well as extracellular fluid distribution. Within the first five minutes following agent administration the concentration of activity in the heart was greater than that of mixed venous blood indicating rapid equilibration of the agent across myocardial cell membranes. The liver concentrated the agent and excreted it into the bile.

What is claimed is:

1. Compounds of the formula:

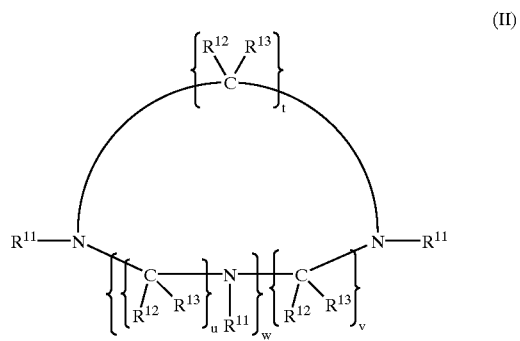

(II)

wherein, t, u and v are each independently 2 or 3;

w is an integer of from 1 to 4;

$R^{12}$ and $R^{13}$ are each independently selected from the group consisting of H, alkyl, alkenyl, aryl, arylalkyl, alkoxy, alkylthio, alkenoxy, alkenylthio, aryloxy, arylthio, alkyl interrupted by one or more oxa, alkenyl interrupted by one or more oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, halogen substituted versions thereof;

$R^{11}$ is a member selected from the group consisting of $R^{12}$, $R^{13}$ and radicals of formula:

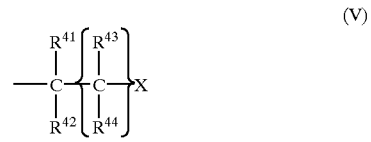

(V)

wherein, $R^{41}$, $R^{42}$ and $R^{43}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen substituted versions thereof;

$R^{44}$ is a member selected from the group consisting of H, hydroxy, amino, alkyl, alkyl interrupted by oxa, alkoxy, aryl, aryloxyalkyl, alkoxyaryl, and halogen substituted versions thereof;

n is zero or 1; and

X is a member selected from the group consisting of alkyl, alkenyl, aryl, arylalkyl, alkoxy, alkylthio, alkenoxy, aryloxy, arylthio, alkyl interrupted by one or more oxa, alkenyl interrupted by one or more oxa, alkyl interrupted by one or more thia, alkenyl interrupted by one or more thia, aryloxyalkyl, alkoxyaryl, aminoalkyl, aminoalkenyl, aminoaryl, aminoarylalkyl, hydroxyalkyl, hydroxyalkenyl, hydroxyaryl hydroxyarylalkyl, halogen substituted versions of each of the above, and radicals selected from the group consisting of:

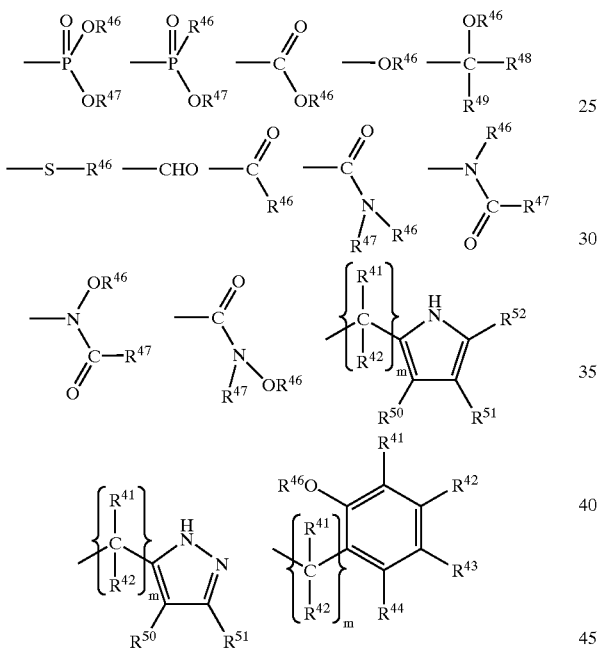

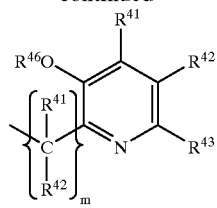

wherein $R^{41}$, $R^{42}$, $R^{43}$ and $R^{44}$ are each independently as described above;

$R^{46}$ and $R^{47}$ are each independently selected from the group consisting of H, alkyl and aryl, or taken together form a divalent linking group between the atoms to which they are attached, thereby forming a ring structure;

$R^{48}$ and $R^{49}$ are each independently selected from the group consisting of H, alkyl, aryl, alkoxy, alkyl interrupted by oxa, aryloxyalkyl, alkoxyaryl, and halogen substituted versions thereof;

$R^{50}$, $R^{51}$ and $R^{52}$ are each independently selected from the group consisting of H, alkyl, alkenyl, aryl, arylalkyl, alkyloxy, alkylthio, alkenyloxy, alkenylthio, aryloxy, arylthio, aminoalkyl, aminoalkenyl, aminoaryl, aminoarylalkyl, hydroxyalkyl, hydroxyalkenyl, hydroxyaryl, and hydroxyarylalkyl; and m is an integer of from 1 to 3;

and wherein at least two of said $R^{11}$ groups comprise at least two contiguous carbon atoms directly attached to nitrogen atoms and the carbon atom in a position β to the nitrogen atom is substituted with a hydroxy and at least one member selected from the group consisting of hydroxymethyl, alkoxymethyl, alkenoxymethyl, aryloxymethyl and combinations thereof;

and wherein, optionally, any two of $R^{11}$, $R^{12}$, and $R^{13}$ are combined to form a ring structure; and dimers thereof, said dimers being formed by the covalent attachment of two compounds of formula (I) through a linking group having from 1 to 6 carbon atoms;

and physiological salts thereof, with the proviso that the molecular weight of said compound does not exceed 2000.

2. A compound in accordance with claim 1, wherein the cation of said physiological salts is sodium or N-methyl glucamine.

* * * * *